(12) United States Patent
Evans et al.

(10) Patent No.: US 8,114,161 B2
(45) Date of Patent: Feb. 14, 2012

(54) SYSTEM AND DEVICES FOR THE REPAIR OF A VERTEBRAL DISC DEFECT

(75) Inventors: Douglas G. Evans, Downingtown, PA (US); Jeffrey C. Kelly, Downingtown, PA (US); Gino Bradica, Ewing, NJ (US); Michael K. Carouge, West Chester, PA (US); Brian Oeffinger, Philadelphia, PA (US)

(73) Assignee: Kensey Nash Corporation, Exton, PA (US)

( * ) Notice: Subject to any disclaimer, the term of this patent is extended or adjusted under 35 U.S.C. 154(b) by 1726 days.

(21) Appl. No.: 11/356,785

(22) Filed: Feb. 17, 2006

(65) Prior Publication Data

US 2006/0253132 A1    Nov. 9, 2006

Related U.S. Application Data

(63) Continuation of application No. PCT/US2006/004073, filed on Feb. 6, 2006, which is a continuation-in-part of application No. 11/123,604, filed on May 6, 2005.

(51) Int. Cl.
*A61F 2/44* (2006.01)
(52) U.S. Cl. .................................................. 623/17.16
(58) Field of Classification Search .... 623/17.11–17.16; 606/139, 142, 143, 144, 148, 151, 154, 185, 606/230, 232
See application file for complete search history.

(56) References Cited

U.S. PATENT DOCUMENTS

| | | | |
|---|---|---|---|
| 4,235,238 A | 11/1980 | Ogiu et al. | |
| 4,472,840 A | 9/1984 | Jefferies | |
| 4,563,489 A | 1/1986 | Urist | |
| 4,669,473 A | 6/1987 | Richards et al. | |
| 4,678,470 A | 7/1987 | Nashef et al. | |
| 4,741,330 A | 5/1988 | Hayhurst | |
| 4,750,492 A | 6/1988 | Jacobs | |
| 5,021,059 A | 6/1991 | Kensey et al. | |
| 5,041,129 A | 8/1991 | Hayhurst | |
| 5,269,809 A | 12/1993 | Hayhurst et al. | |
| 5,545,178 A | 8/1996 | Kensey et al. | |
| 6,056,772 A * | 5/2000 | Bonutti | 606/232 |
| 6,136,010 A | 10/2000 | Modesitt et al. | |
| 6,162,192 A * | 12/2000 | Cragg et al. | 604/15 |
| 6,180,605 B1 | 1/2001 | Chen et al. | |
| 6,180,606 B1 | 1/2001 | Chen et al. | |
| 6,224,630 B1 | 5/2001 | Bao et al. | |
| 6,245,107 B1 | 6/2001 | Ferree | |
| 6,371,990 B1 | 4/2002 | Ferree | |
| 6,402,750 B1 | 6/2002 | Atkinson et al. | |
| 6,428,576 B1 | 8/2002 | Haldimann | |

(Continued)

FOREIGN PATENT DOCUMENTS

WO    WO0195818    12/2001

(Continued)

*Primary Examiner* — Anu Ramana
(74) *Attorney, Agent, or Firm* — Jeffrey R. Ramberg

(57) ABSTRACT

A system for repairing a vertebral disc defect, such as hernia or bulge, a full or partial tear in the annulus, or a weakened annulus wall as a result of an excision procedure. The system introduces a treatment device arranged to repair the defect, and may prevent the leakage of fluid from the nucleus. The components of the device may be resorbable materials, and may induce the ingrowth of cellular material into the components. The system may feature a locating device to ensure proper placement of the treatment device.

34 Claims, 13 Drawing Sheets

U.S. PATENT DOCUMENTS

| | | |
|---|---|---|
| 6,482,235 B1 * | 11/2002 | Lambrecht et al. ......... 623/17.16 |
| 6,508,839 B1 | 1/2003 | Lambrecht et al. |
| 6,530,933 B1 | 3/2003 | Yeung et al. |
| 6,579,291 B1 | 6/2003 | Keith et al. |
| 6,592,625 B2 | 7/2003 | Cauthen |
| 6,626,916 B1 | 9/2003 | Yeung et al. |
| 6,805,695 B2 | 10/2004 | Keith et al. |
| 6,821,276 B2 * | 11/2004 | Lambrecht et al. ............. 606/45 |
| 6,835,205 B2 | 12/2004 | Atkinson et al. |
| 6,955,683 B2 * | 10/2005 | Bonutti ......................... 606/232 |
| 2002/0151980 A1 | 10/2002 | Cauthen |
| 2003/0074075 A1 | 4/2003 | Thomas et al. |
| 2003/0220693 A1 | 11/2003 | Cauthen, III |
| 2004/0097980 A1 | 5/2004 | Ferree |

FOREIGN PATENT DOCUMENTS

| | | |
|---|---|---|
| WO | WO2005020859 | 10/2005 |

* cited by examiner

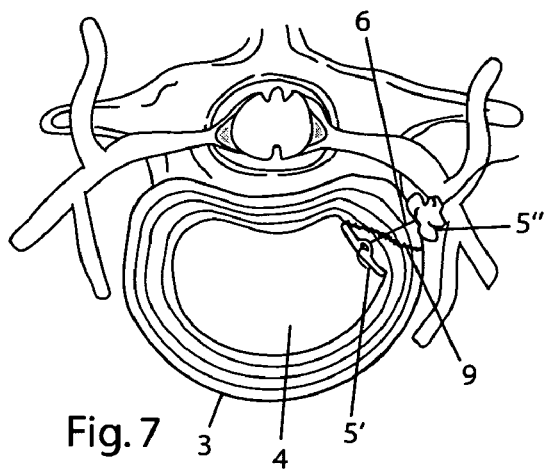
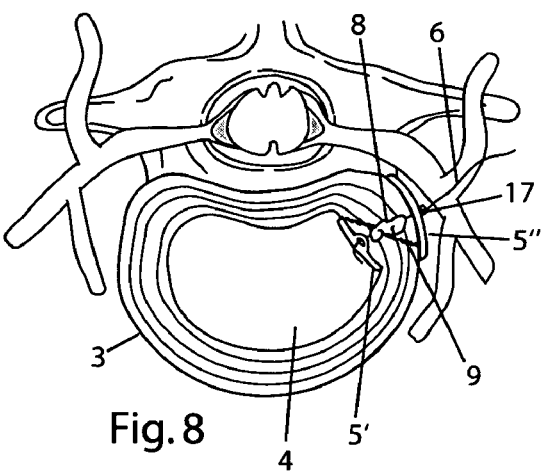
Fig. 7   Fig. 8
Fig. 9
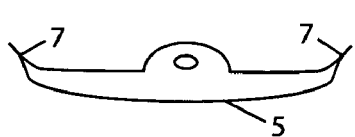 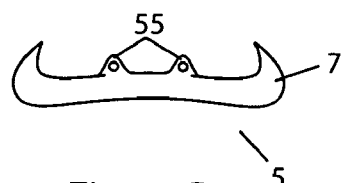
Fig. 10A   Fig. 10B
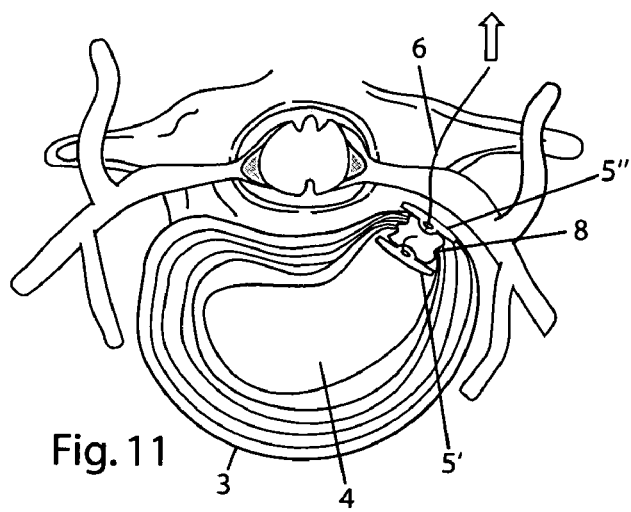
Fig. 11

SYSTEM AND DEVICES FOR THE REPAIR OF A VERTEBRAL DISC DEFECT

RELATED APPLICATIONS

This application is a Continuation of PCT International Patent Application S.N. PCT/US06/04073, filed on Feb. 6, 2006, and designating the U.S., entitled "System And Devices For The Repair Of A Vertebral Disc Defect", which is a Continuation-in-Part of U.S. patent application Ser. No. 11/123,604, filed on May 6, 2005, entitled "System And Devices For The Repair Of A Vertebral Disc Defect", both of which are assigned to the same assignee as this invention, and whose disclosures are incorporated by reference herein.

BACKGROUND OF THE INVENTION

The invention relates generally to methods and devices for human surgery, and in particular these methods and devices may be useful for spinal surgery. More particularly, certain embodiments of the invention relate to devices and methods for treating injuries, defects or surgical procedures associated with the intervertebral disc.

Injuries to the human spine and subsequent pain are one of the most prevalent debilitating conditions affecting the human population. For many of those affected, no position can ease the pain or discomfort associated with spinal injuries or deformities. Such spine related pain can lead to decreased productivity due to loss of work hours, addiction to pain-killing drugs, emotional distress, and prolonged hospital stays. The economic impact of such problems is significant. One common cause for many instances of chronic pain is the bulging, or herniation of the intervertebral disc.

The intervertebral disc is made of two parts, a tough collagen outer layer, known as the annulus fibrosus (hereinafter also referred to as "AF" or "annulus"), and a soft central core known as the nucleus pulposus. The annulus fibrosus is composed of numerous concentric rings or layers of fibrocartilaginous tissue. Fibers in each ring cross diagonally, and the rings attach to each other with additional radial fibers. The rings are thicker anteriorly (ventrally) than posteriorly (dorsally). The nucleus pulposus (hereinafter also referred to as "NP" or "nucleus") is a gelatinous material, which forms the center of the disc. The discs tend to vary in size and shape with their position in the spine. The nucleus pulposus is composed of a loose, nonoriented, collagen fibril framework supporting a network of cells resembling fibrocytes and chondrocytes. This entire structure is embedded in a gelatinous matrix of various glucosaminoglycans, water, and salts. This material is usually under considerable pressure and is restrained by the annulus.

A tear or weakening in the layers of the annulus fibrosus portion of the disc can allow the soft center portion of the disc (the nucleus) to leak out of the annulus, alternatively, the weakened annulus may simply bulge. A ruptured disc may allow the leaking nucleus propulsus material to press up against a spinal nerve root or spinal cord, causing pain, numbness, tingling and/or weakness in a person's extremities. Herniated discs may occur at any level of the spine, but are more common in the lumbar area, followed in frequency of occurrence by the thoracic region and cervical region. Weakening or tearing of the annulus fibrosus may also result in bulging of the annulus fibrosus due to pressure of the nucleus pulposus against the annulus. The bulging tissue may also impinge upon the nerve root or spinal column, causing pain.

The traditional surgical method for treating a damaged, bulging, or herniated disc involves tissue removing procedures to relieve the impingement of the annulus fibrosus or the nucleus pulposus from the surrounding nerves. The procedure is commonly known as a discectomy, and consists of the removal of at least a portion of the disc; it may be performed in an open procedure, a minimally invasive procedure, or an endoscopically assisted procedure. These procedures generally result in a large defect of the annulus fibrosus and in a certain percentage of cases, may lead to progressive degradation of the disc, both nucleus pulposus and annulus fibrosus, lysthesis of adjacent vertebral bodies, stenosis of the nerve canals and increases in related pain symptoms. A means of mechanically and/or biologically repairing the annulus fibrosus may delay or prevent this degeneration cascade of the disc.

Newer technologies and procedures, such as nucleus replacement with injectable or solid prosthetic nucleus devices may also result in a breach in the otherwise coherent annulus fibrosis. In these cases, it is desirable to mechanically close, or otherwise repair the defect in the annulus created to insert the prosthetic material and prevent such material from leakage and extravasation.

The annulus fibrosis (AF) of the intervertebral spinal disc is a lamellar configuration of collagen layers intended to maintain the soft viscous internal nucleus propulsus (NP), provide for motion and linkage of the adjacent vertebral bodies (VB). Certain degenerative or pathologic changes may occur either within the NP which can lead to over stress of the AF and subsequent damage to or tearing of the AF. If left untreated, herniation of the NP may occur, most importantly, the herniation may progress posteriorly toward the spinal cord and major nerve roots. The most common resulting symptoms are pain radiating along a compressed nerve and low back pain, both of which can be crippling for the patient. The AF may also be torn through traumatic injury, which can lead to progressive degenerative changes and herniation or ultimately listhesis of the adjacent VB.

Herniation may be caused by, or be the result of weakening in the AF. Secondary to physiologic changes of the AF or NP, the AF may weaken and protrude from its normal anatomic space, similar to an air bubble bulge in a car tire, or in more severe cases, the AF may tear and allow extravasation of the NP contents to the surrounding anatomy. Symptoms may arise when the herniation or leakage of the NP impinges on the nerve root or spinal cord. There are therapies currently utilized for treatment of the herniation of a vertebral disc, and the resultant pain, starting with conservative therapies such as bed rest and pain medicines, to more invasive therapies, such as epidural injections, open or minimally invasive discectomies or aggressive therapies, such as complete discectomy and fusion of the disc space and adjacent vertebrae.

The prior art describes various procedures and devices for repairing damage to the vertebral disc. The prior art describes repairing a herniated disk by various means, including prosthetic implants, and stressed members. For example, in U.S. Pat. No. 6,805,695, Keith et al. disclose devices and methods of reinforcing an annulus of the disc by introducing a circumferential reinforcement member around the annulus of the disc, or through the annulus and nucleus of the disc.

In U.S. Pat. No. 6,371,990, Ferree discloses an apparatus and method for repairing annular tears and the prevention of further annular tears. Ferree seeks to control vertebral motion by augmenting the annulus with an implant, thereby minimizing the opportunity for annular tears. The augmenting implant is described as being a mesh that may be stapled into the interior of the annulus.

Ferree also discloses in U.S. Patent Application 2004/0097980 an expandable material to fill a defect in a disk, and that the material may be anchored to the annulus with respect to the void filled. In an embodiment, the anchors are described as penetrating through the outer wall of the disc and serve to hold the flexible implant material in place.

Yeung discloses in U.S. Pat. No. 6,530,933 a method and apparatus for herniated disc repair using resilient fastener elements that are implanted and spring back to an original shape to apply tension through gripping elements to hold tightly to the annulus. In an alternative embodiment, the annulus repair technique utilizes a suture affixed to a dumbbell shaped rod to serve as an anchor. The anchor is placed against the outside surface of the annulus, and the suture extends across the interior of the vertebral disc through the nucleus propulsus and out the other side of the disk, such that tension may placed against the disc to repair the hernia, and the tension may be maintained through the use of a washer and suture locking element, such as a knot. With this alternative embodiment, a sealing material may optionally be placed underneath the washer.

In U.S. Pat. No. 6,592,625, Cauthen describes annular repair or reconstruction by insertion of a collapsible patch into the subannular space, whereupon the patch expands to fill the gap and seal off the opening from the escape of nucleus material. Cauthen describes his device as being useful to restore integrity after damage or discectomy to alleviate a herniated vertebral disc; Cauthen does not obviate the need for the discectomy procedure to repair a herniated disc.

In U.S. Pat. No. 6,224,630, Bao describes the repair of an intervertebral disc using an expandable porous material that is inserted into an aperture, and subsequently becomes more permanently secured as the ingrowth of tissue into the pores is actively facilitated. Bao creates a device having a tamponade effect where the swelling of the material provides securement and does not describe a more secure mechanical anchorage using a rigid component in combination with a tissue regenerative material.

The prior art also describes various methods for sealing a percutaneous closure, for example, Kensey et al. in U.S. Pat. No. 5,545,178 describe a system for sealing a puncture made through skin and having a tract extending through to underlying tissue. The puncture closure system consists of an anchor introduced into the underlying tissue and having a filament attached thereto, the filament extends out from the puncture, and facilitates the introduction of a plug material into the tract, whereupon tension is maintained through the use of a holding member. Kensey et al. does not describe the sealing of multiple sites through the employment of a single device, nor is the employment of multiple anchors or plugs on a single filament described.

The prior art does not describe a device wherein the device may be capable of being implanted arthroscopically, among other methods known in the art, and is arranged to prevent the escape of nucleus propulsus from a defect in the annulus, while providing supporting and secured sealing means in a single device, and the device may be capable of preserving normal annulus geometry.

Accordingly, there is a need for a device capable of meeting these and other objectives, wherein the device provides support and secure sealing means for a defect as well as the ability for cellular infiltration and subsequent repair occurring in or created in the annulus fibrosis. Furthermore, there is a need for a device capable of preserving or restoring normal annulus geometry (e.g., repairing a herniated disc), wherein there is support and secured sealing provided at each point of penetration or defect in the annulus.

It is the intent of this invention to overcome these and other shortcomings of the prior art.

SUMMARY OF THE INVENTION

Various embodiments of the current invention strive to overcome these various shortcomings in the prior art. These embodiments allow for singular devices, or combinations of anchors or fastening devices which provide support for the annulus, while sealing the annulus, restoring or maintaining satisfactory disc geometry and providing the scaffold for regeneration of the damaged annulus.

Certain of these embodiments have anchors which may be deployed on both sides of the annulus wall, thereby creating and exerting pressure on the wall. This pressure alone may serve to support and/or seal the annulus; however, the anchors themselves may feature or further be utilized in combination with a sealing means (e.g., elastic biomaterials, patches, collagen, etc.) that may be beneficial or necessary to aid sealing. The various embodiments of the invention contemplate the use of a variety of devices including, but not limited to, patches, plugs, staples, expandable materials, meshes, anchors, sutures, flowable materials, sealants, glues, gels and other wound and tissue repair devices known in the art.

Several embodiments of the present disclosure utilize at least one sealing means. The sealing means, or sealing member, as the terms are used interchangeably herein, may be most beneficial if placed at the inside wall of the annulus or on the outside of the wall depending on the geometry of the device, the type of sealing means, and the geometry of the affected anatomy. Furthermore, the seal may be placed proximal or distal to the fastening device(s). It is recognized that the force internal to the annulus (i.e., the force from the fluid nucleus propulsus) may assist sealing by pressing the sealing means against the annulus, where such sealing means may be preferably located internal to the annulus.

Overall disc or annulus geometry may be beneficially altered by placing a fastening device at or through a distal wall of the annulus, while placing a second fastening device at or through the proximal wall, where the devices are connected, e.g., by a tether, suture, flexible, or rigid member. This type of device would allow compression to be placed across each disc wall, while simultaneously compressing or restraining the disc across its diameter. Again, sealing means may be employed, as previously discussed.

These various embodiments may be particularly useful in the situation where the annulus is torn. Since the annulus is fibrous, tears generally occur in the circumferential direction (i.e., not purely radial) along at least a portion of the fibers. Deploying a fastening device across the tear could cause compression to be placed across the torn annulus surfaces, thereby allowing the combination of securement and friction (thereby restricting movement of the torn surfaces against each other) to hold and support the annulus.

Commonly, discectomies or laminectomies are performed to relieve pain. These embodiments may augment, if not replace these types of procedures. That is, multiple fasteners, or a single through-wall fastener, may be placed proximal and distal to the annulus entry tract (in the case of a discectomy), and a sealing patch may be placed adjacent either fastener, or the sealing patch may reside mid-wall to the annulus.

It is also recognized that a sealing member may function as a fastener itself, thereby minimizing the number of device components, procedural steps, and/or procedural time. To that end, a sealing member may be rigid, compliant, or elastic; furthermore, the sealing member may be a composite of various materials, which are best suited for support and sealing functions. As a non-limiting example, such fasteners may be comprised of a rigid polymeric backing material (which may or may not be resorbable, e.g., PLA or polyurethane)

which has a layer that contacts the tissue which comprises a malleable material, which may or may not be resorbable (e.g. polymer, collagen, etc.) to seal the tear or procedurally made opening. Such components may be comprised of materials inherently radiopaque or treated with substances which make them radiopaque when viewed under standard imaging techniques to allow the surgeon to visualize placement.

These various embodiments may be at least partially made from permanent or biodegradable materials such as those listed in Table 1, and these devices may have a secondary or tertiary effect by the delivery of drugs or biologics such as those listed in Table 2. In an embodiment of a fastening or sealing device made from the materials described above, once implanted in a living being, the device may cause or induce the new growth or regrowth of cellular material. In this embodiment, the material encourages the ingrowth of cellular material that securely integrates the device into the surrounding tissues, thereby repairing the weakened area in a more effective manner.

In the embodiment where the device is a resorbable material, the ingrowth of cellular material into the device allows for a permanent repair upon complete resorption of the resorbable device, as the material is replaced by the growth of cells to create a natural tissue material similar to and integrated with the surrounding structures.

In the embodiment where the device is a non-resorbable material, the ingrowth of cellular material into the device allows the complete integration of the device with the surrounding tissue, thereby creating a suitable repair having nearly similar compliance and other physical characteristics as the original tissue material.

Procedurally, these various embodiments may be delivered from posterior or anterior directions, based on the anatomical constraints as well as, among other things, herniation, disease, or type and geometry of the defect. While it is envisioned that similar, if not the same, delivery devices and methods may work for posterior as well as anterior procedures and placements, certain types of procedures may benefit greatly from devices or embodiments which sense their location or detect where they are located in the anatomy. For many annulus repair devices it may be beneficial to utilize minimally invasive methodologies to position the device. Minimally invasive procedures utilize laproscopic or endoscopic instruments to perform procedures through small openings in a patient's skin and can result in less trauma and faster healing times for the patient. However, such approaches are challenging in that the physician may not be able to directly visualize many aspects of the procedure. It has been discovered through experimentation in ex-vivo models that several embodiments of the devices of this invention can benefit by using delivery systems that can locate the transition between the annulus and the adjacent tissues to ensure proper device placement.

Location detection devices are known in the art, for example U.S. Pat. No. 5,282,827, assigned to the assignee of the present disclosure, may be used to accurately place a hemostasis device in an artery (delivery of a hemostasis device using a location detector) also assigned to the assignee of the present disclosure. However, while these aforementioned devices may perform suitably for the currently contemplated procedures, certain modifications could improve their performance. That is, the annulus propulsus, as well as certain of the surrounding fluid, is normally more viscous and less able to flow to provide the "perceptible signal" of the aforementioned patents.

In order to improve upon these previous embodiments, the location detection means incorporated in the current embodiments may further comprise instrumentation or other features allowing for accurate placement of the device percutaneously. Such instruments may be calibrated at some portion so as to allow the surgeon to determine the exact thickness or dimension of the spinal disc component to be traversed with the fixation device. These placement instruments can also be comprised of an actual depth measurement instrument whereby the surgeon can engage the aspect of the disc to which the distal most portion of the device should engage and then determine the traversing distance. A location detection means may also beneficially stabilize the delivery system for the placement of a repair device in an intervertebral disk.

In order to effectuate the proper placement of the various devices of the present invention, one may optionally employ various accessory instruments. For example, it may be beneficial to employ, for example, tools to determine the appropriate depth and size of the defect, tools that effectively dissect tissues at or adjacent to the defect in order to prepare an area for accepting the device, or tools that sever a suture or connecting element after a deployment of the device, such that excess suture length will not cause irritation to nearby tissues.

DESCRIPTION OF THE DRAWINGS

FIGS. 4-8, and 11. Depiction of the placement of various closure or treatment devices of the present invention.

FIGS. 9, 10A and 10B. Exemplary depictions of an anchoring member with and without barbs, and having one or more attachment points for receiving connector elements.

DETAILED DESCRIPTION OF PREFERRED EMBODIMENTS

Figure 1:
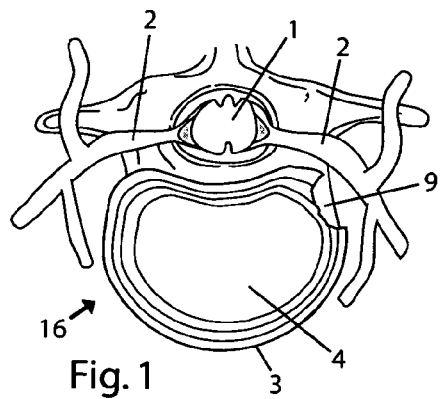
FIGS. 1-3. Depicts overhead cross-sectional views of a vertebral disc having a defect therein, in the form of an annulus wall having a reduced thickness, a partial tear, and a full tear.

Repair of Tears of the Annulus Fibrosis

The annulus fibrosis (AF) of the intervertebral spinal disc is a lamellar configuration of collagen layers intended to maintain the soft viscous internal nucleus propulsus (NP), provide for motion and linkage of the adjacent vertebral bodies (VB). Certain degenerative or pathologic changes may occur either within the NP or the AF which can lead to over stress of the AF and subsequent damage to or tearing of the AF. If left untreated, herniation of the NP may occur through the tear, and most importantly, the herniation may progress posteriorly toward the spinal cord and major nerve roots. The most commonly resulting symptoms are pain radiating along a compressed nerve and low back pain, both of which can be crippling for the patient. The AF may also be torn through traumatic injury, which can lead to progressive degenerative changes and herniation or ultimately listhesis of the adjacent VB.

An embodiment of the present invention is intended to provide means by which the AF can be compressed, e.g., along, or across, as appropriate, the axis of tear, thereby preventing the potential herniation of the NP through the tear and resultant pain.

Any or all of the embodiments of the present invention may beneficially incorporate a location detection means that is capable of providing for accurate positioning and placement of the device by sensing or otherwise allowing the detection of the location of the device within the anatomy. More specifically, the location detection means may allow the detection of the location of the device in order to ensure the proper placement of the components of the device within the annulus, nucleus, and/or the interface between the annulus and nucleus. Additionally, the location detection means may also serve as a locking member to maintain a position of at least a portion of the device with respect to the body.

Various methods disclosed herein could be used for such purposes. One embodiment would include the use of an expanding balloon, an articulating wing or finger, or a retractable element (e.g., footplate, finger, wing, etc.) to locate the interface between the nucleus and annulus, and assure proper placement of the closure or treatment device. By way of example, a delivery tube or access cannula could have an expandable or reconfigurable member (e.g. balloon, anchor, finger, etc.) that can be used to help locate the transition between the annulus and nucleus or other adjacent tissues. Such expandable members could help, among other things, provide an indication of proper depth and location for device placement, provide an indication of proper device size needed for the particular defect opening, and further provide a physical space into which a device can be implanted. The system could be advanced into the appropriate tissue and then the expandable, reconfigurable, or retractable element could be activated, so that the device could be withdrawn, advanced, or otherwise manipulated until an indicator provides a signal that the device is at a desirable location. Concepts of this approach could employ "tactile feel" as one indicator, to sense when a delivery system is at the appropriate location. Similarly, sensors or mechanical means, may be utilized at or near the distal end of the device to confirm placement, such as an optical sensor or pressure sensor that may be exposed to tissue during placement of the device, and enable confirmation of accurate placement of the device.

Additionally, a location detector means may further serve to provide an indication of the size of the defect to be repaired. For example, a device (e.g., footplate) of known dimensions could be inserted through the defect while maintained in an orientation that presents a narrower profile. Once through the defect, the device may be deployed and withdrawn towards the operator, thereby providing feedback to the operator as to that particular device would be capable of effecting the necessary repair of the defect. This procedure may be repeated, varying the known dimension of the device, until an adequate size of the necessary device is determined (i.e. a device that will not be pulled through the defect while under tension). It may be beneficial to minimize the size of the device inserted into the defect, in order to minimize complications from the procedure.

It is recognized that such an expandable or reconfigurable member may also beneficially serve to stabilize the disc, and or the components of the invention during and after placement of the device. Additionally, other stabilizing components may be utilized to achieve proper placement of the device, such as a sliding ring, flange, or other component that may be delivered following the insertion of a delivery tube or sheath, and placed against the target site, or the surrounding tissues to lend stability to the device. As can be seen with reference to FIGS. 36-46, and to be discussed in further detail below, the expandable member may be expanded against the annulus interior wall, thereby preventing the retraction of the positioning device from the nucleus, and stabilizing the positioning member. Optionally, a slidable flange may be advanced along the body of the positioning device in order to apply securing pressure against the exterior of the annulus, or other tissue, thereby maintaining the accurate placement of the positioning device. The flange may be advanced by external application of force, or alternatively, may be advanced by operation of an advancing mechanism, such that the slidable flange is directed towards the distal end of the positioning device.

In another embodiment of a location detection means, a cannula or access sheath may be provided having a separate pathway (e.g. a lumen) for providing a location probe. The separate pathway may have an exit port located at or near the distal end of the delivery system. A flexible or reconfigurable member may be extended, either through the device, or from the device, and allow the surgeon to gauge the nature of the tissue, such as through tactile feel. A member being inserted into nucleus propulsus material would relay tactile information that the tissue is soft, as it would easily yield to advancement of the probe. In contrast, the tough fibrous annulus material would provide greater resistance to the advancement of the probe, affording similar confirmation of placement of the device.

In these and other embodiments, the location detection means may rely on calibrated insertable components, such as needles, delivery sheaths, or cannulas, which may be provided having graduated markings to indicate depth of penetration, and allow proper placement of the repairing components of the device.

It is also recognized that the use of markers or bands (e.g. radiographic markers, visual markers, etc.) may provide location information for any of the described embodiments, such as through the use of radiographic techniques (e.g. MRI, X-ray, etc.), and further aid in ensuring the proper placement of the device of the present invention.

Figure 2:
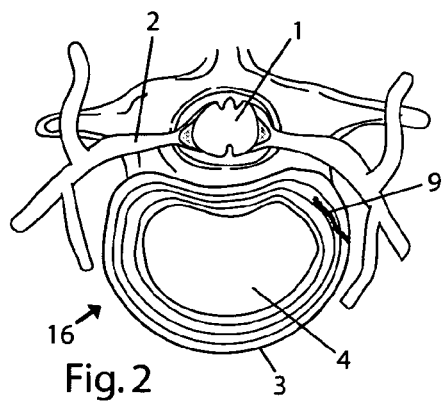
Figure 3:
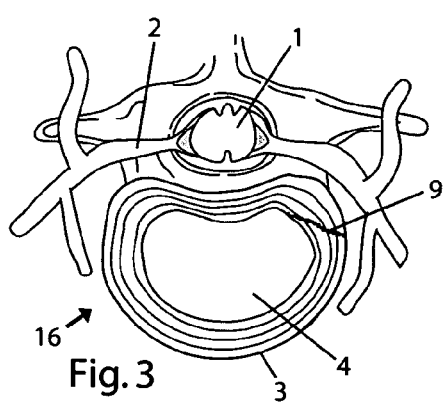
Figure 4:
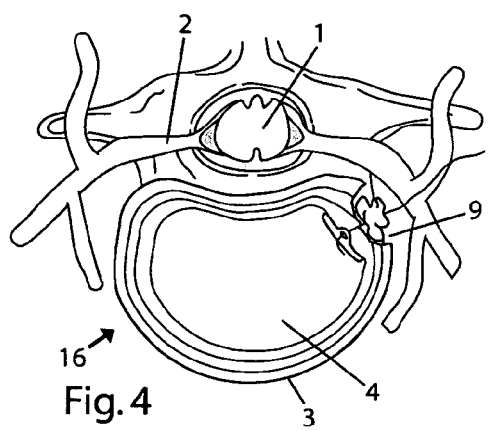
Figure 5:
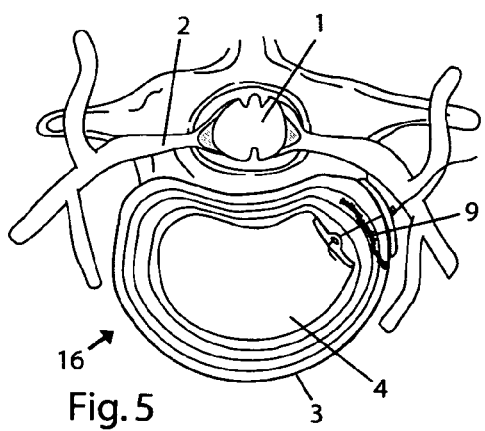

FIG. 1 shows a transverse section of the intervertebral disc space between two adjacent vertebral bodies. The intervertebral disc 16 contains the annulus fibrosis (AF) 3, which surrounds a central nucleus propulsus (NP) 4. Also shown in this figure are the spinal cord 1 and the nerve roots 2. In FIG. 1, the annulus is depicted having a defect 9 therein, wherein the thickness of the annular wall is reduced, as may occur through, for example, a full or partial discectomy procedure, where the removal of at least a portion of the annular wall may be necessary, commonly to minimize the effects of herniated discs. With reference to FIGS. 2 and 3, the defect 9 may be in the form of an annular tear, as depicted by the solid black line through the AF, as may occur in the course of surgical procedures, injury, or natural degradation of the annulus fibrosus. A defect, as used herein, refers to any variation or anomaly from the normal presentation of the annulus, and the term is deemed to include, for example, full or partial tears, full or partial excisions, holes, bulges, degradation, thinning, hyperplasia, or thickening of or in the annulus material. As will be described more fully below, the damage or defect 9 depicted in FIGS. 1, 2 and 3 may be repaired in various manners through the practice of the present invention, for example as can be seen respectively in FIGS. 4, 5, and either of 6 or 7.

In order to repair these defects, whether full or partial, the device of the present invention may serve to fill the defect and/or apply compression to the annular wall. Furthermore, the present invention may serve to reinforce the defect area, thereby preventing further herniation. The defect 9 created by a discectomy procedure may fully penetrate the annulus, extending through to the nucleus propulsus, and forms an opening in the annulus, requiring repair in order to prevent the extraversion of the nucleus.

In some embodiments of the present invention, as shown in FIGS. 5, 6, 7, and 8, the device is intended to apply and maintain a compressive force between the outer and inner aspects of the AF 3 at the point where the defect or tear 9 exists, thereby serving as a treatment device to facilitate healing. With reference to FIG. 8, one embodiment of the implanted device consists of an anchoring element, or footplate 5 placed internally of the annulus, which is connected to a second footplate 5, placed externally to the annulus, and connected by means of a connecting member 6. The connecting member may preferably be a suture, filament, thread, fabric, or other flexible member. Alternatively, the connecting member may be a rigid member capable of resisting the free movement of associated anchor elements or sealing members, and intermediary materials. The rigid connector element may be capable of resisting an encountered force, and also serve to maintain tension upon the tissue restrained by the treatment device. The connecting member may be manufactured from materials known in the art, e.g., synthetic polymers, natural polymers, metal, etc., and may be resorbable or non-resorbable. The footplates 5 may be constructed of a biocompatible material (e.g., resorbable polymer, resorbable collagen or other resorbable or non-resorbable material). The footplates as used in the practice of the present invention may be arranged to serve as an anchoring means for the device, and optionally may serve as a sealing means. The footplates may be rigid, or somewhat flexible, but in any event, not so flexible as to pull through a defect or delivery opening in the AF when implemented, an example of which is depicted in FIG. 9. The implantable components (e.g., the footplates, sealing members, connecting elements, intermediary components, fastening elements, etc.) of the present invention may be manufactured from a variety of biocompatible, resorbable or non-resorbable, materials, examples of which can be found in a non-exhaustive list supplied as Table 1 below.

As can be seen in FIG. 9 and FIGS. 10A and B, the footplates 5 may also contain small barbs or points 7 to interface with the internal or external surface of the AF to aid in securing the device and prevent them from being dislodged. It is recognized that footplates may be specifically shaped for a particular purpose, that is, footplates intended to be inserted into the interior of the annular wall may have a first orientation, shape, or curvature, while another footplate intended for use outside of the annular wall may feature a second orientation, shape or curvature. It is also recognized that the footplate may have a connector element (e.g. suture) affixed in a manner that is centered on one surface of the device (as can bee seen in FIGS. 9 and 10A), or alternatively may be affixed off-center (as depicted in FIG. 10B). In the embodiment shown in FIG. 10B, multiple connector element attachment points 55 may be employed, where each is employed off-center. The embodiment utilizing off-center connector element attachment locations may utilize active deployment, that is, where upon delivery, the rotation of the device is assisted by the off-center location of the connector element applying the retractive force, thereby causing the rotation of the footplate into position. Further tension may be applied without causing rotation by applying and maintaining tension upon the connector elements, urging the footplate or barbs against the tissue.

It is also recognized that various arrangements of footplates and connecting members may be necessary. For example, it might be beneficial to utilize a single footplate on the exterior of the annulus, and place a plurality of footplates in the interior of the annulus, all connected by at least one connecting member, or alternatively, the arrangement may be reversed, with a single interior footplate and a plurality of exterior footplates. It is recognized that the footplates described above may additionally feature some application (e.g. coating) of a sealing material (to be discussed below) to aid in maintaining annulus integrity against leakage. The footplates, or other members, may also contain a marker, additive, or other material that can be visualized with x-ray or other imaging technologies to assist with the placement of the device and potentially allow for longer term follow-up of the device location.

In an embodiment of the present invention having a tear in the annular wall, as depicted in FIG. 8, though it is recognized that a partial tear or other defects would behave similarly, there is arranged, between and affixed to (e.g., glued, knotted, etc.) the footplates 5 (both internal and external) by any means known in the art, an intermediate member 8. The intermediate member may be located at the level of the defect 9 and may be made from a natural polymer, (e.g., collagen, etc.). In some embodiments of the present invention, the intermediate component may serve to deliver a therapy (e.g. for the purpose of moderating inflammatory response, aiding healing, etc.), such as a biologically active agent, examples of which are listed in Table 2. The intermediate component 8 may consist of a flowable or expandable material (e.g. hydrogel, adhesive, packing material, etc.) that serves to aid in sealing or adhering the tissue, so as to prevent the flow of material into or out of the NP (e.g., loss of NP, or inflow of blood, etc.) through the defect in the AF (e.g. a plug). This may be accomplished by providing an intermediate component 8 that is able to conform to the shapes and surfaces of the defect. It is recognized that the intermediate component may be delivered as a rigid material that is able to swell upon being implanted in the body, effectively sealing the defect from the extravasation of nucleus material. The intermediate member may additionally feature a natural material that can act as a matrix for cellular infiltration and regeneration of the annulus.

The materials of the present invention that are resorbable may comprise a porous tissue matrix material (PTM). This PTM material will preferably have an interconnected porosity, and sized to encourage the invasive growth of new cellular material. The interconnected porosity also serves to ensure adequate fluid flow to provide an optimal growth environment for the invasive cells. The ingrowth of new cellular material will beneficially encourage the incorporation of the device material into the nearby tissues, and provide for biomatching or compliance matching, where the device material and components present similar physical characteristics as the original tissue.

Figure 6:
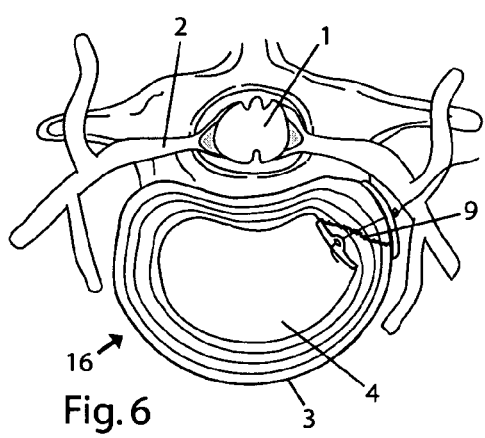

In another embodiment, as depicted in FIG. 6, arranged through the annular wall is the connecting member 6, without any intermediate or plugging material. It is recognized the connecting member may itself be coated or treated to aid in healing. For example, the intermediate component may feature a coating or otherwise release (e.g., by natural degradation, diffusion, etc.) a therapy (e.g. biologically active agent, drug, etc.), where the therapy may prevent an undesirable response or promote a beneficial response. In the embodiment shown in FIG. 6, the tension maintained by the placement of the closure device serves to repair the defect, and or allow for healing to occur.

In another embodiment, as depicted in FIG. 7, a footplate 5 may be placed internally to the annular wall 3, connected to a connecting member 6, extending through the wall and associated with an external footplate 5" or anchor in the form of a sealing plug, which may be similar in nature to the sealing material described previously. This sealing plug may beneficially be a non-rigid material, however, the physical characteristics of the sealing plug are such that it will not be pulled through the annular wall once implanted but may be urged into the annulus (e.g. by the tension applied through the connecting member 6), and may deform to fill the defect, such as may be created through an excission procedure. For example, the footplate may be a sealing plug of hydrophilic material which, upon hydration, expands in volume to form a thick mass, at least rigid or viscous enough so as to prevent pull through, yet deformable enough to adequately seal against the annular wall, thereby preventing the escape of nucleus therethrough. Additionally, the plug may swell causing the plug material to intimately contact the surrounding tissue to promote cellular infiltration and migration into the implanted material to heal the annulus tissue. In another embodiment, the sealing material may be in the form of a tapered mass of material, such that tension maintained via a connector element urges the tapered mass further into the defect opening, which due to the constraints of the defect size, serves to maintain the sealing plug in place and effectively seals the opening.

Figure 48:
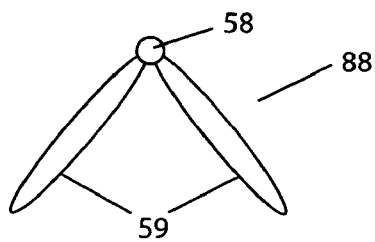
FIGS. 48 and 49. Depiction of alternative embodiments of a plugging or sealing material.

Other embodiments of the sealing plug material may incorporate a hinged design, as shown in FIG. 48, depicting plug 88 having a hinge 58 or other folding means known in the art, and multiple arms 59, such that the plug material 88 can be implanted while in a folded state, and subsequently, the hinge would open, allowing the plug to effectively seal the opening. It is recognized that the plug 88 could be hinged in a manner that the open end could face either towards or against the nucleus pulposus material, though preferably the hinge is arranged such that any pressure from the nucleus would act to further open the hinged plug, thereby increasing the effectiveness of the seal against the annular wall. Preferably, the hinge mechanism 58 is capable of preventing the fold from becoming reversed, such as might occur if opened beyond 180 degrees, as subsequently the plug material could more easily be ejected from the opening. In an embodiment having more than 2 arms, the plug may open up around the hinge in a fashion similar to an umbrella, and may have a fabric or other material extending between radial arms which will help prevent the escape of nucleus material or other tissue.

Figure 49:
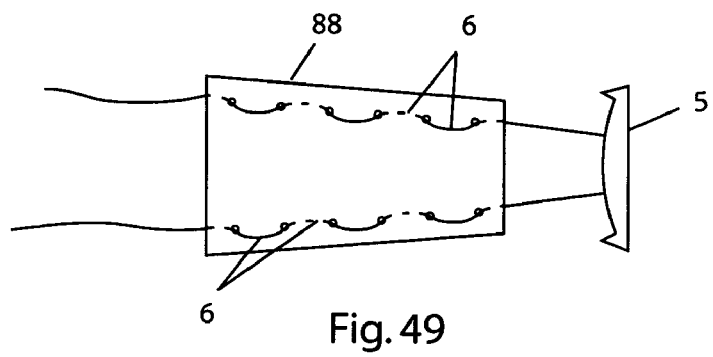

Alternatively, another plug material embodiment is shown in FIG. 49, where the plug 88 has an overall cylindrical shape, which may or may not be tapered, allowing it to fit a variety of sizes. The plug material 88 may be introduced against or into the defect of the wall, and preferably serves to pinch a portion of the annulus wall between the distal end (away from the operator) of the plug 88 and the inner anchor or footplate 5, thereby achieving an adequate seal to prevent the escape of nucleus material. As discussed previously, the plug material 88 may be non-rigid, such that applying tension by the sutures or connector elements 6 might cause the plug material to fold in on itself repeatedly, causing the plug to become plicated, similar to the pleats of an accordion. Each of the pleats may then affect the overall shape of the plug material, causing an effective increase in girth, while collapsing in length, and additionally lending increased flexibility, such that the plug 88 may conform more readily to the defect, and limit the migration of the device or escape of nucleus material. Furthermore, any folds or pleats of the plugging material may serve to trap annular tissue between the folds, thereby increasing the effectiveness of the seal. In practice, folds of the pleated embodiment of the plug material may also serve to create increased surface area having intimate contact with the surrounding tissue to promote cellular infiltration. Furthermore, the folded pleats may serve to create a laminar effect, which mimics the natural layering of the annulus, and may aid in the regeneration of the annular tissue.

It is recognized that the plug material need not necessarily be capable of folding, and may be applied as a tapered or cylindrical material, that physically occludes the defect opening.

Referring to FIG. 11, where the defect 9 extends fully through the annular wall, and may be created as a consequence of a full discectomy, the intermediate component 8 is preferably capable of filling the entire defect void created by the removal of a portion of the annulus. The intermediate component may be locked in place, and against adjacent walls of the annulus by an applied pressure created through compression applied through the connecting member.

Figure 12:
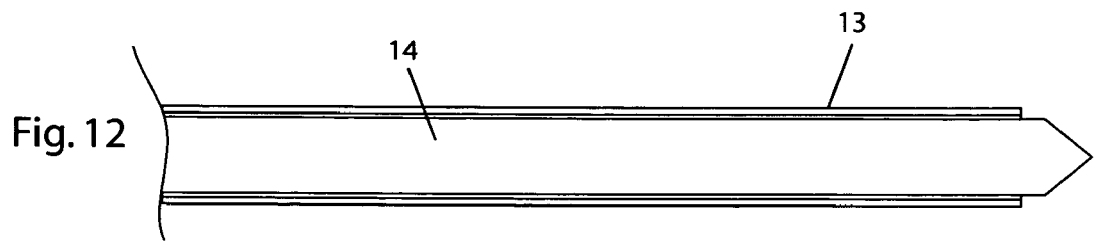
FIG. 12. Cross sectional depiction of a cannula and obturator for the implementation of the present invention.

In practicing the present invention for the repair of a partial or full defect in the annular wall 3, an access sheath (e.g. a cannula) 13, optionally housing an obturator 14, as depicted in FIG. 12 may be inserted through a percutaneous incision in the external skin and extended through underlying tissue to the AF using techniques known in the art.

In an embodiment, the access sheath 13 through which any subsequent instruments or components may be inserted is preferably of a fixed length. The subsequent instruments which may be directed through the sheath may incorporate that fixed length into their shafts, and extend out the distal end of the sheath by a precisely determinably amount, as they may be calibrated or have markings, in order to allow the surgeon to determine the depth of penetration into the target tissue (e.g., into the disc, thickness of the annulus, and zone of nucleus). As the sheath and obturator are directed to the target site, the obturator may be removed and a trocar or tissue dilator (for example, tissue dilator 18 of FIG. 36) is used to initially penetrate into the AF at the zone of the defect or tear. A sharp trocar or tissue dilator (which is preferably calibrated along at least a portion of its length) may be inserted through the access sheath 13 to the surface of the AF at the location of the tear and confirmed in some manner (e.g., via radiography). It is envisioned that multiple increasing diameters and/or lengths of trocars or tissue dilators may be used to gradually open a lumen within the AF. The instruments inserted into the living being, (e.g. the sheath, trocar, and obturator, etc.) may feature monitoring elements (e.g., radiopaque markers, bands, penetration markers, orientation markers, calibration, etc.) to allow accurate tracking, placement and implementation of the devices using techniques known in the art (fluoroscopy, x-ray visualization, etc.). The trocar may then be advanced into the disc, for example through the AF to the level of the NP. The trocar may then be removed, thereby creating an accessible open lumen within the cannula or access sheath 13, such that the delivery device 15 of FIG. 13 containing an embodiment of the treatment device, such as a fastener or closure device may be inserted into and extend through the access sheath 13 as depicted in FIG. 14. As shown here, the treatment device or closure device of FIG. 13 includes a distal anchor 5' attached to a connecting element 6, and a proximal anchor 5" here depicted in the form of a material capable of sealing or plugging the defect upon deployment. In another embodiment, the sealing or plugging material may be an intermediary component that is located between a second anchor (not shown) which would be housed within the delivery device 15 in a position proximal to the intermediary element, and extended between the proximal anchor, the intermediary material and the distal anchor would be a connector element arranged to facilitate the application of tension upon delivery. As depicted in FIG. 14, the fastener or closure device within the delivery device 15 includes a pair of anchoring elements (5' and 5") and a connecting element 6 extending therebetween. Also shown is a fastening element or holding mechanism 17 which may be, for example, a slip knot that is arranged to secure the device and maintain tension after it is applied through connecting member 6. It is recognized that multiple arrangements of the fastener or closure device are possible by varying the arrangements, lengths and numbers of the closure device elements in and around the tissues being repaired. That is, multiple anchors 5 may be deployed internal to the nucleus, and multiple connecting elements 6 and optionally intermediary materials 8 may be utilized to secure the elements in or around the disc and annulus.

FIG. 14 depicts the delivery device 15 within the access sheath 13, and is prepared for being introduced into the disc through percutaneous puncture, and extended into an aperture created in the AF to the level of the NP for delivery and implementation of the remaining components of the device (e.g. the closure device elements). In an embodiment, the delivery device 15 may be calibrated along its proximal end relative to the proximal edge of the access sheath 13 to allow the surgeon to determine when the anchor element 5' has traversed a distance approximately equal to the thickness of the AF. Alternatively, other location detection mechanisms may be utilized in ensuring accurate placement of the delivery device for placement of a fastener or closure device.

Figure 13:
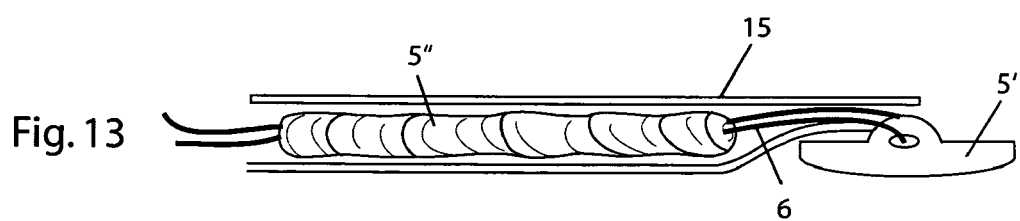
FIG. 13. Partial cross-section of embodiments of the delivery device and treatment device of the present invention.
Figure 14:
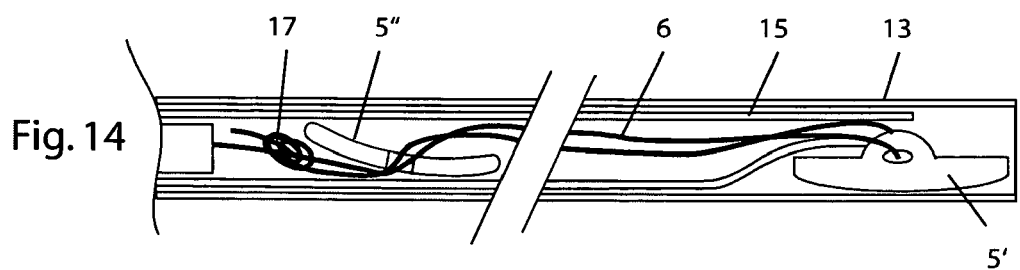
FIG. 14. Another embodiment of the treatment device and delivery device, housed within the access sheath.

With reference to FIGS. 13 and 14, the delivery device 15 may be shaped or incorporate elements that ensure the device (e.g. anchor, patch, mesh, plug, etc.) once deployed, is unable to be retracted back into either the access sheath or the delivery device. For example, in one embodiment, the anchor may be maintained temporarily in alignment with the axis of the delivery device, however, once free from the restraining confines of the access sheath 13 and/or delivery device 15, the anchors 5 will naturally shift, or alternatively actively deploy, to a position that precludes retraction back into its aligned position. This may be accomplished in various manners, such through the flexibility of the connecting element 6, or alternatively may rely on a restrictive element (e.g., nitinol fingers or other one way componentry shaped into the delivery device) that allow passage in one direction but prevents passage in the reverse direction. As discussed previously, with reference to FIG. 10B, the anchor 5 may actively deploy as tension is applied to a connector element that may be attached off-centered to the anchor. These methodologies may serve to ensure that the anchor 5' of the closure device is deployed properly on the first attempt, and prevent the anchor 5' and the balance of the closure device from reentering the sheath 13 or device 15, and also prevent the entire closure device from being retracted along with the access sheath 13 and/or delivery device 15. In this manner, the need for further tamping or ejecting mechanisms to ensure the placement of the closure device may be eliminated. Though, especially in the absence of these features, it is recognized that the present invention may be compatible with the use of such tamping or ejecting mechanisms, such as a rod extended down through the delivery device to eject the closure device elements.

For example, in order to accomplish the delivery of the device intended for use in repairing a full or partial tear 9 in the annular wall 3, for example as depicted in FIGS. 6, 7 or 8, once the delivery device 15 and access sheath 13 of FIG. 14 is internal to the AF 3 (within the nucleus 4 region), a first footplate 5' may be deployed, such as through the implementation of a device or tamping mechanism directed through the internal bore of the delivery device 15 to deliver (e.g. push) the implantable device components out of the distal end of the delivery device and/or access sheath 13, and contacted against the internal aspect of the AF 4. The location of the footplate 5 or other components of the device may be confirmed by imaging as they may be made of, or incorporate a radiopaque material. Subsequently, the connecting member 6, and optionally an intermediate component 8, of the device may be deployed through the aperture to the level of the tear 9. As previously described, the intermediate component 8 may be made of suitable packing material, e.g., collagen, alginate, etc., and may contain some bioactive substance both of which either together or alone act to improve the healing of the tear. Next, the proximal footplate 5" and optionally sealing material may be deployed against the outer surface of the AF 3 and compression may be applied to the AF through the deployment of a holding mechanism or fastening element 17 (e.g. a slip knot, or other method for maintaining tension between the footplates as known in the art) which is drawn thereby against the proximal footplate 5". The deployment of a holding mechanism 17 may be performed with or without the delivery device 15 in place, using techniques known in the art. It is recognized the act of compression alone may act to facilitate the healing of the tear, or may act to prevent herniation or leakage of the contents of the NP through the tear, or prevent further expansion of the tear. The internal coupling mechanism or connector element 6 which may be made of a bioabsorbable material is then removed or cut at a convenient location, such as at the surface of the skin.

Figure 15:
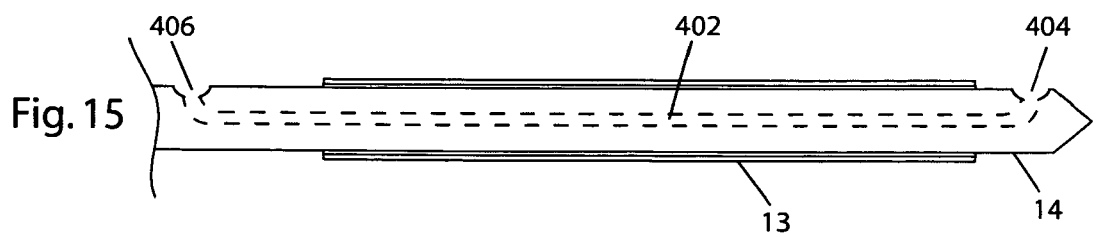
FIG. 15. A cannula and access sheath of the present invention incorporating a location detector means.

In this or another embodiment, the use of a means for location detection may be beneficial. In FIG. 15 there is shown embodiment of a locating device for effecting the proper positioning of the access sheath 13 or other deliver device within the annulus or nucleus. As can be seen in FIG. 15, the depicted embodiment of a locating device basically comprises a conventional obturator 14 providing a passageway 402 extending longitudinally down substantially the length of the device, preferably internal to the obturator, although external may be capable of functioning similarly. In the embodiment having an internal passageway lumen 402, a detection port 404 extends radially inward into the device communicating with the distal end of the passageway 402, while a proximal port 406 extends radially inward into the device communicating with the proximal end of the passageway 402. The locating device is arranged such that it may be fully inserted within the access sheath 13 and extend a precise amount beyond the end of the access sheath, as shown in FIG. 15, and further the proximal port does not enter the proximal end of access sheath 13, thereby ensuring that proximal port 406 remains accessible or visible to the operator.

The length of the annular passageway 402 is selected so that when the obturator 14 of the locating device shown in FIG. 15 is fully extended within the access sheath 13 and the distal end of the sheath is located within the interior of the annulus or lumen, the detection port 404 of the passageway 402 extends just beyond the free end of the sheath, while the entrance port 406 is accessible to the operator. The detection port 404 forms a window, which is exposed to the material in the annulus.

In another embodiment of the location detector of FIG. 15, a flexible or reconfigurable member (e.g. a probe)(not shown), may be inserted into proximal port 406 and extended through the passageway 402, exiting at detection port 404, such that the flexible probe or member may be used to probe the tissue, thereby using, for example, tactile feel to locate the sheath or other insertion member, such that a device may subsequently be accurately placed.

In another embodiment of the location detector of FIG. 15, a reduced pressure (relative to that of the nucleus material), aspirating force, or vacuum may exist or be applied at proximal port 406, such that the passageway 402 is under negative pressure or reduced pressure relative to the pressure of the tissue material at the distal end and detection port 404. The reduced pressure or aspiration may cause the tissue adjacent to the detection port 404 to be introduced into the passageway 402. Continued aspiration may cause the tissue to travel the length of the passageway and exit at proximal port 406. In the event that the detection port 404 is adjacent annular material, the fibrous nature and inherent strength of the annulus will prevent aspiration and/or detection of material at the proximal port. By contrast, where the tissue adjacent the detection port 404 is a gelatinous or liquid material, the tissue will travel the length of the passageway 402, and be detectable at the proximal port 406. In this manner, the locating means may thereby serve to indicate the location of the detection window 404, allowing the determination of the location of the distal end of the access sheath 13, whether it has penetrated into the nucleus or remains in the annulus. It is recognized that, especially with younger patients, the nucleus material may be capable of freely flowing through such a passageway 402 as described above, while at atmospheric pressures, though as the nucleus material ages or degrades, it tends to become more viscous, and may resist flowing through such a passageway, thereby necessitating application of a vacuum.

In another embodiment of a location detector, sensors (not shown) may be placed at or near the distal end, such as within detection port 404 to confirm accurate placement. Such sensors may be in the form of an optical sensor or pressure sensor that may be exposed to the tissue or fluid during placement of the device, and generate an indicator signal or other feedback for the operator and enable confirmation of accurate placement of the device.

Repair of Herniated or Bulging Annulus Fibrosis

Figure 16:
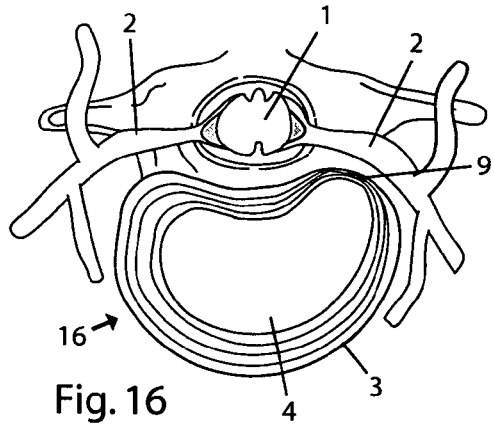
FIGS. 16 and 17. Depicts overhead cross-sectional views of a vertebral disc having a defect therein, in the form of a hernia or bulge in the annulus, having an intact annulus or extravasation of the nucleus.
Figure 17:
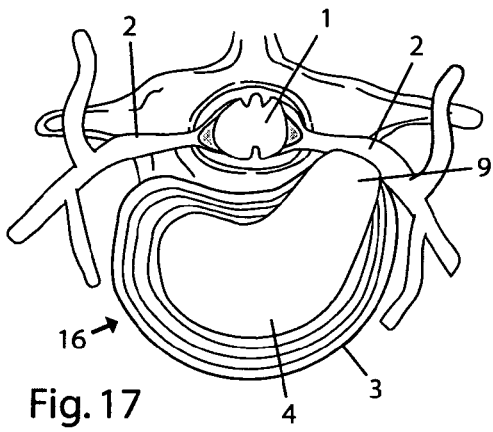

An annular defect such as a bulge or herniation may be caused by or be the result of weakening in the AF secondary to physiologic changes to the AF or NP, and the AF may weaken and protrude from its normal anatomic space pushed by the internal NP as can be seen in FIG. 16. In more severe cases, the AF 3 may rupture and allow extravasation of the NP 4 contents to the surrounding anatomy (as depicted in FIG. 17). Symptoms may arise when the herniation (bulge) or leakage of the NP through the defect 9 in the AF 3 impinges on the nerve root 2 or spinal cord 1. There are many therapies currently utilized for treatment of the herniation (bulge) and resultant pain, starting with conservative therapies such as bed rest and pain medicines, to epidural injections, to open or minimally invasive discectomies or to complete discectomy and fusion of the disc space and adjacent vertebrae. An object of this invention is to provide a minimally invasive means to contain leakage or to reduce the bulge or defect 9 created by one of the invasive treatment means in an annulus to prevent impingement on the nerve roots or spinal canal.

Figure 18:
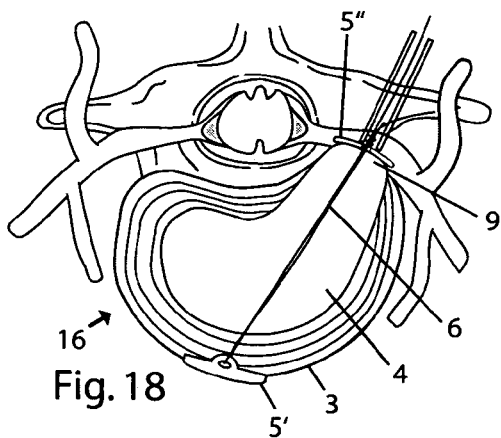
FIGS. 18-24. Depiction of the placement of various closure or treatment devices of the present invention.
Figure 19:
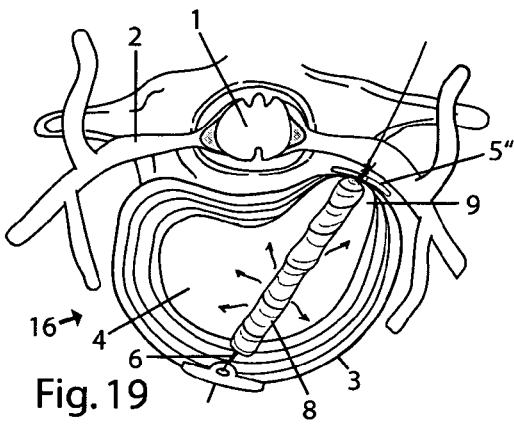

In an embodiment of the device envisioned for the treatment of bulging or herniated discs, with reference to FIG. 18, the closure device consists of a distal footplate 5' which is arranged to rest against the external aspect of the AF 3 directly opposite the bulge 9 in disc 16 in the anterior-lateral portion of the AF 3. A connecting element 6 traversing through the NP 4, connects the distal footplate 5' to another footplate, proximal footplate 5", which is arranged to rest against the bulge 9 in the affected part of the AF 3 in the posterior part of the disc. The footplates 5' & 5", as previously described may be constructed of a resorbable polymer, resorbable collagen or other resorbable or non-resorbable material. The footplates 5' and 5" may be somewhat flexible, but not so much as to pull through the delivery opening or defect 9 upon the application of compression. The footplates 5' and 5" may also contain small barbs or points 7 (as can be seen in FIGS. 10A and B) to interface with the internal or external surface of the AF 3 to prevent dislodging. Connecting member 6 may preferably be a suture, similar to that described above, and may be manufactured from polymers known in the art, including synthetic and natural polymers. In some embodiments of the device, the connecting member may also be associated with an intermediate component 8, as has been described above. The intermediate component 8 may be arranged within the walls of the annulus 4, as shown in FIG. 11, and/or all or a portion of the NP 4, as shown in FIG. 19. The intermediate component 8 may function to prevent the escape of NP through the defects 9 or openings created by the implanting of the closure device. In an embodiment, the intermediate material 8 may be treated with fibrin glue or other means by which it can stick to the opening or defect 9, or alternatively may serve to deliver at least one therapy, drug or biologically active agent, such as those listed in Table 2. It is recognized the suture or connecting member 6 itself may feature a coating of a sealing material or a therapy that may be delivered upon implantation in the living being. All of the closure device components, including footplates 5, intermediary material 8 and connecting members 6 may be non-resorbable for permanent implantation, partially resorbable, or completely resorbable, such that a temporary implant may be achieved.

It is recognized that there may be advantages to presenting footplates 5 of differing dimensions in the device. For example, in the case of repairing a herniated disc, there may be benefit to presenting a distal footplate 5' opposite the bulge or defect 9 that is greater in surface area than a proximal footplate 5" placed directly against the bulge 9. In this manner, as compression is applied through connecting member 6, the compressive force is distributed over a larger area by distal footplate 5', and the corresponding force applied by proximal footplate 5" will accordingly be distributed over a smaller area, resulting in increased efficiency in minimizing the bulge or defect 9 protrusion. Furthermore, multiple footplates at any end of the closure device may be utilized in order to increase the surface area in a similar manner.

Figure 20:
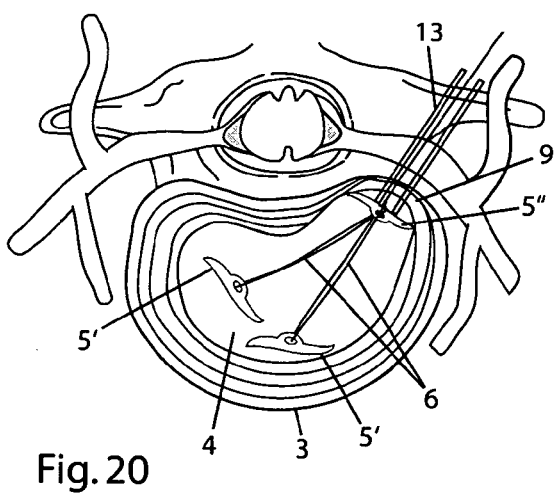

It is also recognized the footplates may be delivered by the delivery device to a variety of locations within the intervertebral disc, wherein one or more footplates may be utilized to provide support for an opposing footplate. The location of the footplates may be in a variety of combinations, including the placement of multiple footplates and/or in multiple locations. For example, one or more of the footplates may be placed within the nucleus as shown in FIG. 20. In the embodiments having footplates placed within the nucleus, they may be relying on the inherent viscosity nucleus propulsus material to provide the necessary resistance and thereby maintaining tension upon a connecting member 6. It is recognized that the viscosity of the nucleus may be significantly increased in aged nucleus material or degraded material. Alternatively, there may be a benefit to placing the footplates within the annular wall, such where the footplates serves to replace a portion of the annulus that has been removed by excission, as shown by the proximal footplate 5" of FIG. 21. Most preferably the footplates may be placed against the exterior aspect of the annulus as described previously, and as shown with reference to FIG. 19.

Figure 21:
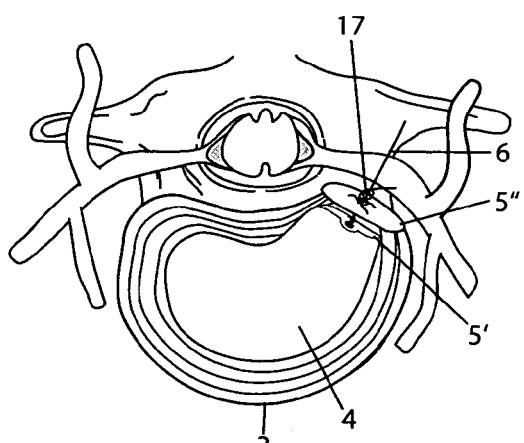
Figure 22:
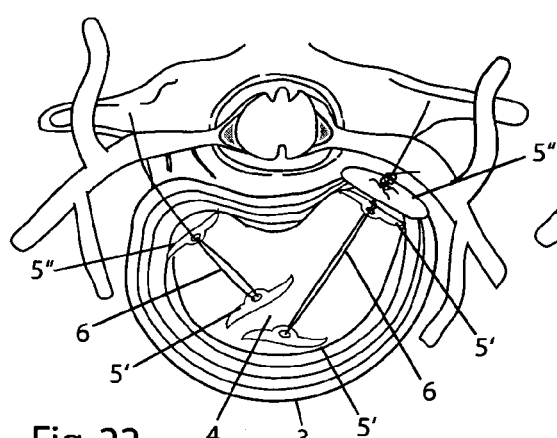
Figure 23:
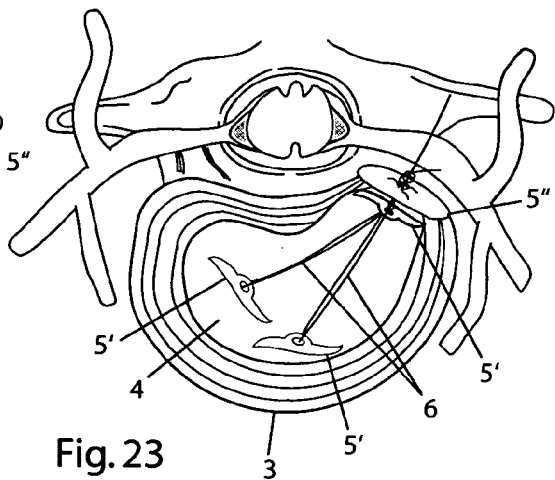

It is recognized that various other combinations of footplate placement are possible, varying in location and number. Footplate locations may vary within a given embodiment, such as is depicted in FIG. 21, having a distal footplate 5' against an interior aspect of the annulus 3 and within the nucleus 4, and having a proximal footplate 5" inside of the annulus or replacing a portion of the annulus. Additionally, in some embodiments, the placement of multiple footplates may be necessary to provide the necessary levels of support. Such multiple footplate placement may be seen in the exemplary embodiment of FIG. 20 where multiple distal footplates 5' are operating in parallel to maintain tension upon connecting members 6 and upon proximal footplate 5". Alternatively, as can be seen with reference to FIG. 23, additional distal footplates 5' may be placed operating in series with another distal footplate 5', which is itself further connected to and arranged to maintain tension upon and a proximal footplate 5". Furthermore, multiple defect sites may be addressed through the practice of multiple embodiments of the present invention, as can be seen in FIG. 22.

Figure 24:
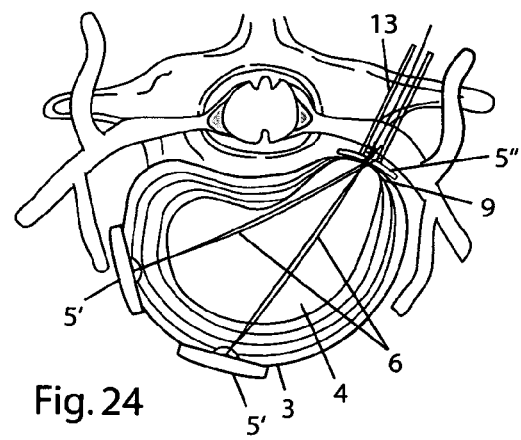

In an alternative embodiment of the device envisioned for the treatment of bulging or herniated discs, as depicted in FIG. 24, the device features multiple anchoring members or footplates 5' which are arranged to rest against the AF opposite the bulge 9 in disc 16 in the anterior-lateral portion of the AF 3. The placement of multiple anchoring members or footplates as shown herein serve to provide increased surface area over which to distribute a given load, which will necessarily be less than the load per unit area imposed by a single similarly sized footplate placed against a bulge or defect 9, thereby overcoming the bulge and restoring the normal appearance of the annulus 3.

With reference to FIGS. 18 and 19, depicting the process for repair of a defect 9 in the form of a hernia (bulge). In practicing this embodiment of the present invention for the repair of a herniated disc or bulge or defect 9 in the annular wall 3, a cannula or access sheath 13 and obturator 14, as described above with reference to repairing a partial or full defect in the annular wall, may be inserted percutaneously and directed towards the annular wall, preferably towards the defect 9 in the annulus. As described previously, once the cannula 13 has passed through the soft tissue and is resting in the proper location against the annulus 3, ideally at the location of the herniation or bulge 9, the obturator 14 is removed and a trocar or tissue dilator 18 may be inserted and may be advanced into and/or through the annulus, thereby creating or expanding an aperture for the insertion of the delivery device. Furthermore, and in the case where the footplate 5' is to be rested against the outer aspect of the opposing portion of the AF 3, the trocar or tissue dilator 18 may be advanced through the opposite AF as well. The insertion of the trocar may be performed using standard techniques known in the art. Upon verification of placement of the trocar completely through the disc 16, such as is possible through the employment of monitoring features such as detection location features (e.g., calibration of the trocar, radiographic visualization, or other means) the delivery device 15 housing the closure device may be inserted through the access sheath 13, and through the nucleus 4 space, exiting the opposite side of the AF.

Once the delivery device has been passed through the AF, NP and opposite AF the deployment of the fastener device is performed to arrive at the embodiment as depicted in FIGS. 18 and 19 having a distal footplate 5' external to the annulus 3.

Alternatively, the delivery device may remain within the NP and not extended out the opposite AF, and may deploy one or more distal footplates 5' against the internal aspect of the AF 3, with the result as depicted in FIG. 20. Deployment may occur by depositing the closure device components into place from the delivery sheath 15, for example, by utilizing a rod or other pushing device directed through the delivery sheath from a proximal location, which upon contacting one or more components of the closure device causes each component to exit the distal end of the delivery sheath. The location of each component of the device may be confirmed by various monitoring mechanisms as known in the art, e.g., radiopaque or other visible markers in combination with x-ray imaging or fluoroscopic imaging, positional markings or bands, etc.

Subsequently, and preferably as the delivery device 15 and/or access sheath 13 is retracted, the connecting member 6, such as a suture may be deployed, optionally in conjunction with a soft intermediate component 8 of the device, as can be seen in FIG. 19. As previously described, the intermediate component 8 may be made of a polymer material, and may be resorbable (e.g., collagen). Furthermore, the intermediate component may contain some bioactive substance, therapy, or drug, such as those listed in Table 2. It is recognized that any of the resorbable or non-resorbable components utilized in the practice of the invention may also beneficially delivery a biologically active agent as well, such as pain reducing or inflammatory reducing agents, or other drugs. The intermediate component 8 including any bioactive substance, either together, or alone, may act to improve the healing of the defect. It is recognized the intermediate component 8 may be made of a rigid polymer similar to the footplate 5. Compression may be applied to the AF 3 and the bulge defect 9 upon removal of the delivery device 15 and/or annular sheath 13 from the disc 16, and deployment of holding mechanism or fastening element 17 (e.g., an automatic slip knot) which when pushed against the proximal footplate 5", or in the case of a rigid intermediary component, the holding element may be pushed against the intermediary component 8, and maintains tension upon the connecting member 6. This tension results in compression created between footplates 5' and 5", such that the act of compression alone may act to reduce the bulge defect 9 in the AF 3, thereby relieving or preventing impingement on the nerve root 2 or spinal cord 1, and resulting pain or harm. Additionally, the implanted fastener or closure device may act to prevent subsequent extravasation of the contents of the NP 4 through the bulge or defect 9, and may provide a scaffold, such as may occur if made of a collagen or other porous material, to support the regeneration of the AF. The internal connector or coupling mechanism 6, extending out from the disk proximally may then be removed at a convenient location to encourage healing, e.g., such as being severed at the surface of the skin, in order minimizing irritation, inflammatory response and opportunity for infection.

Repair of the Annulus Fibrosis Secondary to Placement of a Nucleus Propulsus Implant Material Newer approaches to the repair of the degenerated intervertebral disc and specifically the degenerated NP have envisioned the removal, replacement, and/or augmentation of the natural NP material with an artificial nucleus replacement material designed to mimic the natural mechanical properties of the NP. In this manner, normal disc function may be restored by the insertion of a synthetic or natural material through the annulus and into the nucleus.

Figure 29:
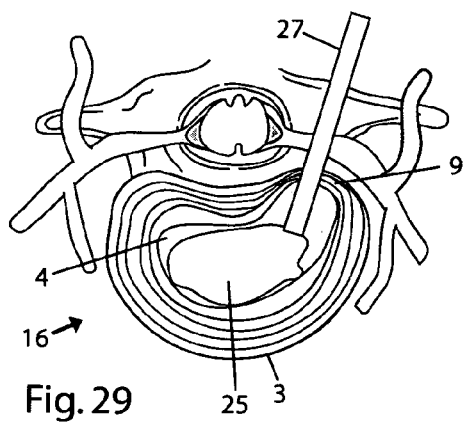
FIG. 29. Depicts overhead cross-sectional views of a vertebral disc having a nucleus implant material placed into the nucleus.

As can be seen in FIG. 29, the nucleus replacement implant material 25 may be a material capable of being delivered by a delivery apparatus 27 (for example, being injected via a needle, cannula or other suitable instrument, or being placed through a cannula, sheath or other suitable instrument), into the region of the nucleus 4, either with, or without removing the existing NP. The material 25 may then remain entrapped, either permanently or temporarily, within the annulus 4, and restore the natural mechanical function of the nucleus propulsus 4. Examples of materials suitable for injecting and serving as a nucleus replacement include synthetic or natural hydrogels (e.g., collagen gels, PEC gel, etc.) Alternatively, an injectable implant material 25 may be injected as a liquid, hydrogel, or paste, and harden or cure in-situ to become a self-supporting implant material 25. This material may serve to supplement the mechanical properties of the degenerated NP, or in the case of complete nucleus removal, the implant material would replace the NP and mimic the natural biomechanical and viscoelastic properties of the disc.

Alternatively, the nucleus implant material 25 may be a self-supporting material, resilient or otherwise (e.g. solids, porous foam, collapsible resilient cage, disc or stent structure, etc.), at the time of being implanted. There are currently several developmental attempts to address this approach, most notably in the form of a device utilizing a partially hydrolyzed polyacrylonitrile housed within a polyethylene jacket (manufactured by Raymedica), and an implant utilizing Aquacryl 90 which is a modified poly-acrylonitrile (PAN) that can take up to 90% of its weight in water (manufactured by Replication Medical). This material is bonded to internal Dacron meshes and is partially hydrated and upon insertion provides anisotropic axial expansion The self-supporting implant material 25 utilized in this embodiment of the present invention may be provided in various shapes or conformations (e.g., collapsed, preshaped to a particular portion of the disc or the entire disc, etc.). The implant material 25 may be implanted in a first conformation, and following implantation take on a second conformation, for example, a collapsible implant may expand after being placed within the nucleus due to physical means or rehydration, and arrive at a second conformation due to the anisotropic properties of the material.

In the practice of the technique of NP replacement or augmentation, the integrity of the natural AF 3 would necessarily be compromised to allow the insertion of the implant material. For example, in order to facilitate delivery of the NP filling implant material 25, and in the case of an injectable implant material 25, a delivery apparatus 27 in the form of a needle may be directed through the soft tissue to the outer level of the AF 3, then through the AF and into the nucleus 4 in order to deliver the implant material 25. The delivery apparatus 27 upon penetrating through the AF, may be directed through an existing defect, or alternatively may create a defect 9, which may or may not require repair through the techniques described herein. It is also a technique that a cannula/obturator may be a suitable delivery apparatus 27 for a nucleus replacement implant material 25, and may be inserted to the level of the AF 3, an opening created either through the placement of multiple trocars through the AF or alternatively through the use of a coring/cutting tool to create a lumen in the AF for the removal of the NP and subsequently for the injection of the material. Alternatively, for a solid implant material 25, an opening in the AF must be created to allow the removal of the degenerated NP and insertion of the implant material. In order to implant solid or self-supporting devices whose size is at or near that required to fill the nuclear space 4, a relatively large opening or defect 9 must be utilized or created in the AF 3 to allow removal of the NP material and insertion of the self-supporting implant material 25. If left un-repaired, there have been reports in the literature of expulsion of such devices. It is recognized that a collapsible or deformable self-supporting implant may serve to minimize the opening required to implant the device. In any event, it is desirable to contemplate the filling and repair of the defect 9 in the AF 3 to reduce the risk of expulsion of the implant material 25 and to support the repair and regeneration of the AF. Furthermore, in order to prevent potential extravasation of the filling material 25 after implantation, and to reinforce the mechanical integrity of the AF 3 or to potentially regenerate the AF, a fastener or closure device of the present invention may be utilized to ensure that the opening created in the AF to deliver the NP filling material is closed, as can be seen with reference to FIG. 11, where the nucleus 4 would be replaced with an implant material (not shown). The implant materials 25 contemplated may utilize natural matricies, which can facilitate or enhance the in-growth of cells and tissue and ultimately facilitate the regeneration of the AF, providing a more natural construct.

Following the implantation of the artificial NP implant material 25 (whether injectable or self-supporting), the fastener or closure device of the present invention may be directed through the same access opening in the annulus through which the injection or insertion occurred, to seal the opening or defect 9. This repair may occur in a substantially similar manner as has been described with reference to any of the techniques described above for repairing a defect in the annulus, particularly the techniques described to treat the defect remaining in a discectomy procedure. These techniques are particularly well suited for repairing defects that are created through the use of injectable nucleus replacement materials. Especially in the case of NP repair or replacement with a solid implant, there may be a need to repair a much larger breach in the AF. This may be accomplished using the present invention to insert a device as depicted in FIGS. 25 and 26, 27, and 28, which are discussed below.

Figure 25:
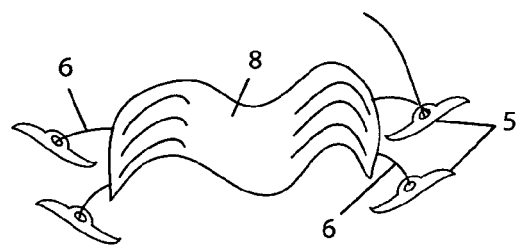
FIG. 25. A depiction of the components of one embodiment of the treatment or closure device of the present invention.

The embodiment of the device depicted in FIG. 25 features a plurality of footplates 5, positioned to prevent the free movement of the closure device, and preferably arranged at the extremities of the implant. Arranged between footplates 5, is at least one connecting member 6 as has already been described. The connecting member 6 may be a single filament that is threaded or extended between each of the footplates 5 of the device. Alternatively, multiple connecting members 6 may be utilized between a pair or more footplates 5. It is also recognized that several connecting members 6 may be arranged between each footplate 5, fastened together (e.g., knotted, etc.) using techniques known in the art, effectively forming a web of connecting members 6.

Also arranged between the footplates 5, and associated with the at least one connecting member 6 is an intermediate component 8 as shown in FIG. 25. This intermediate component 8 may be of similar material and construction to previous embodiments having already been described.

Figure 26:
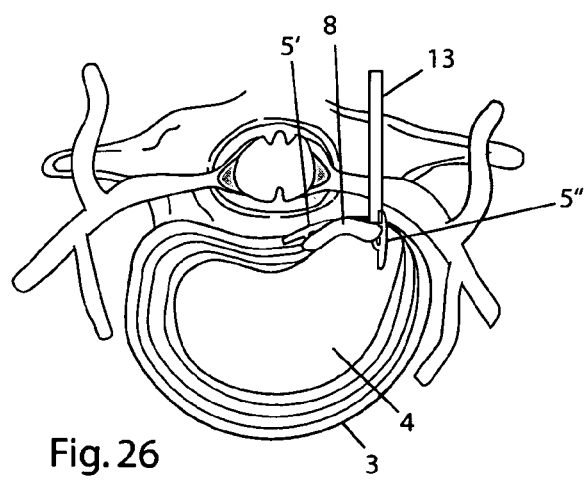
FIGS. 26-28. Depiction of the implanting of the treatment device of FIG. 25.
Figure 27:
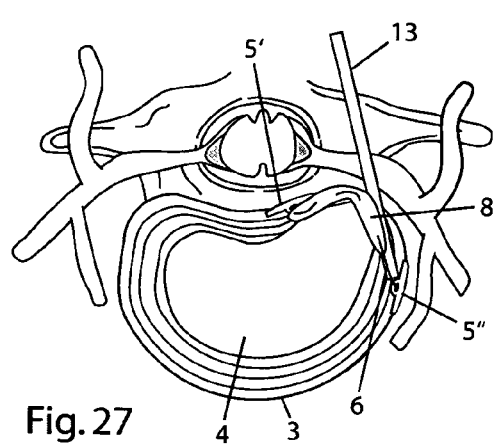
Figure 28:
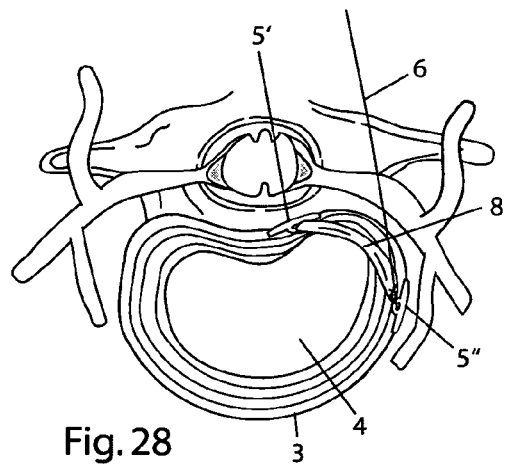

As depicted in FIGS. 26, 27, and 28, the intermediate component 8 may be utilized to supplement or replace a substantial portion of the AF 3, and may be in the form of a sheet of material arranged to replace or repair the portion of the AF that has been damaged, for example, in the insertion of a solid NP replacement implant. The sheet of material may be a resorbable polymer for temporary augmentation or repair of the AF or a resorbable sheet matrix with porosity to allow cellular infiltration and potentially facilitate the regeneration of the AF. Alternatively, the sheet of material may be non-resorbable to effectuate a permanent repair to the AF.

In the practice of the present invention as depicted in FIGS. 26, 27, and 28, access to the NP may be achieved using techniques similar to those described elsewhere in this specification, for example, utilizing any or all of a cannula, obturator, tissue dilator, trocar, access sheath, guidewire or other described components. The deployment of the fastener device to effectuate the repair of the AF may be performed similarly to the repair of a tear or defect in the annulus. Additionally, as depicted in FIG. 26 showing the present invention having an intermediate member 8 in the form of a reinforcing band, a distal footplate 5' may be placed initially against the exterior of the AF or embedded within the AF. The placement of the initial footplate 5' may be performed in a manner similar to the placement of a subsequent additional anchor, here depicted as proximal footplate 5", as depicted in FIG. 27. As depicted, access to the interior of the disc may be achieved by entering directly through a central opening created in the AF, such as may be created through the introduction of NP replacement material, injury or other defect in the AF. Subsequently, and now from within the disc, the access sheath and or the delivery device housing the fastener device is extended through the AF at a separate point from the entry location, and towards the exterior of the disc. Thereupon a first anchor 5' may be deployed, either at a point where the anchor may be deployed internal to the AF, or preferably externally to the AF, such that the anchor may become lodged against the exterior of the AF upon the application of tension or other force. By repeatedly directing the access sheath and/or delivery device through the AF from within, and deploying subsequent anchors or footplates 5' or 5", the delivery of all of the anchors needed for a particular device embodiment may be possible. By directing the access sheath and/or delivery device to place anchors in a pattern into tissue surrounding the central opening through which the trocar originally entered the disc, it may be possible to establish a perimeter to which the interconnecting members 6 and/or intermediate material 8 (e.g. a band or sheet) may be deployed as tension is applied to the connecting member 6 (e.g. a suture) arranged between each of the anchors 5 and optionally associated with the intermediate material 8. Subsequent to placing all of the anchors needed for a particular device, the access sheath and delivery device may be withdrawn from the central opening. The connecting member preferably is left with an end extending out from the disc, such that tension may be applied, as depicted in FIG. 28 to lodge the anchors in place, and extend the intermediate material, such as a band or sheet, within the disc. As described previously, a holding mechanism or fastener element 17, such as a slipknot, or locking button, lock washer, or other device that may be employed to maintain tension upon the device. It is also possible that the intermediate material (e.g., as previously described, and may preferably, in this embodiment include a flexible barrier, mesh, sheet, etc.) can be secured in position with footplates or other anchoring elements (e.g. sutures, staples, glues, etc.) that are secured at other locations not shown in FIGS. 26, 27, and 29.

Figure 30:
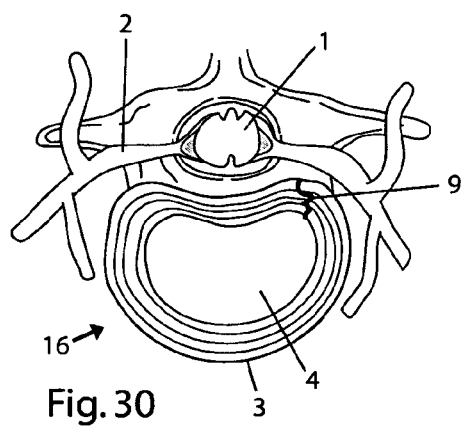
FIG. 30. A cross-sectional view of a vertebrae and disc from above depicting a defect in the annulus.

Description of an Exemplary Procedure for Repair of a Defect in the AF Using the Device of the Present Invention With reference to FIG. 30, there is depicted a typical defect 9 in a vertebral disc 16, here shown as a full tear in the annulus 3. In the practice of the present invention, various techniques known in the art may be utilized for the introduction of the closure device through a delivery device in order to repair such a tear in the annulus. The following description of one delivery technique is for example only, and is not intended to limit the inventor to only this practice, as other similar or equivalent delivery techniques are available and known in the art, and the practice of the present invention through these equivalent procedures is inherent within the description.

Figure 31:
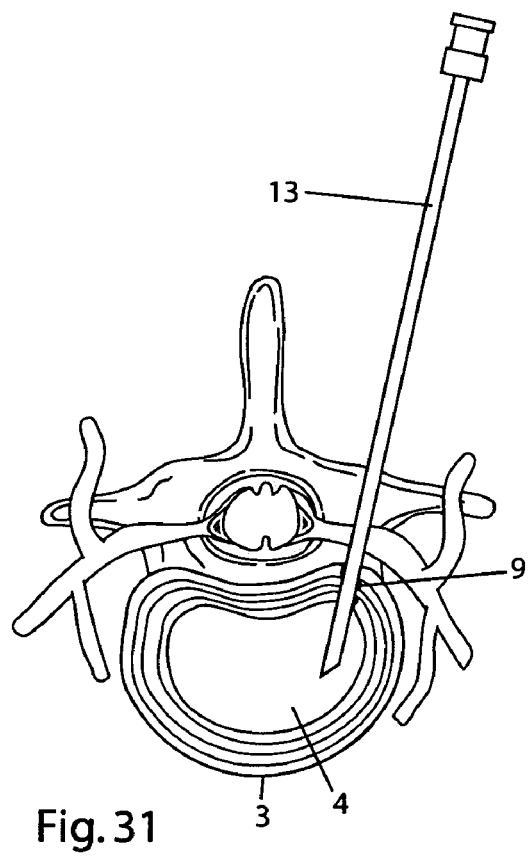
FIG. 31. An access cannula (e.g. needle) positioned into the defect of FIG. 30.
Figure 32:
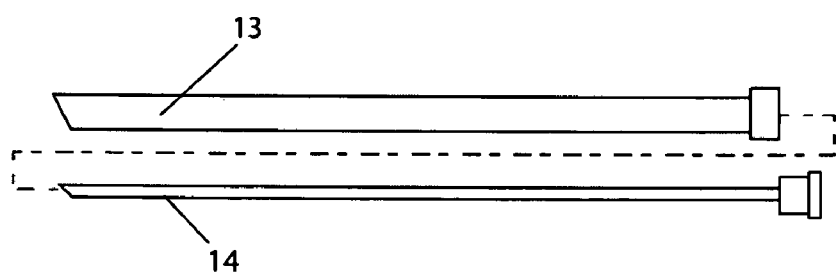
FIG. 32. An exploded profile view of a cannula and obturator.
Figure 33:
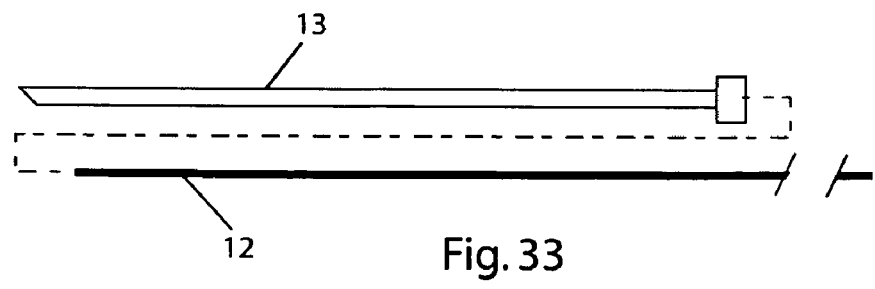
FIG. 33. An exploded profile view of a guidewire and cannula.
Figure 34:
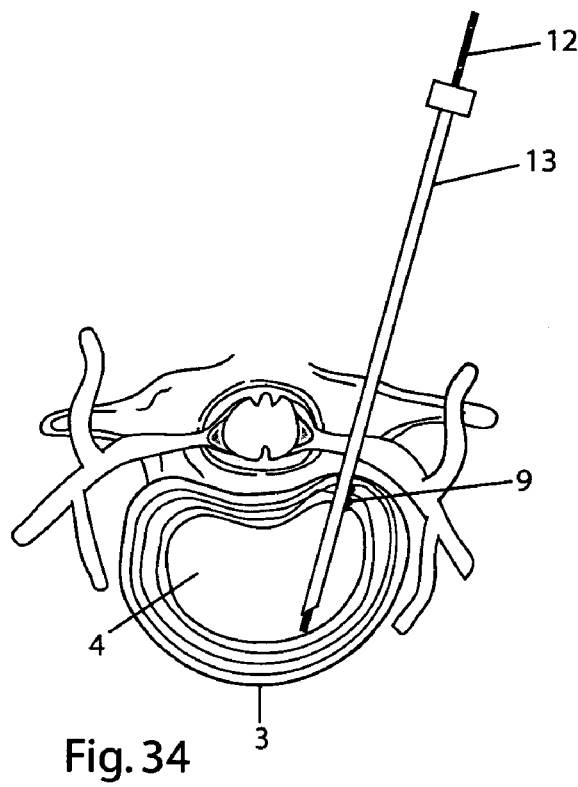
FIG. 34. An elevated view of the Guidewire positioned into the access cannula and directed into the disc of FIG. 31.

As depicted in FIG. 31, an access cannula 13 (e.g. a needle) may be positioned through a defect 9, and extend into the interior of the annulus (i.e. the nucleus propulsus) using standard techniques known in the art, preferably radiographic techniques (e.g. x-ray). As shown in the exploded view of FIG. 32, the cannula 13 may initially have an obturator 14 as shown, which may serve to prevent tissue from entering into the central lumen of the cannula while it is being directed through tissue. Upon insertion of the cannula 13 into the interior of the disc 16, the obturator 14 may be removed, leaving an empty lumen in the cannula 13 for the introduction of the delivery device, as will be discussed. Alternatively a guidewire 12 or other wire-like element may be introduced into the cannula (as can be seen in exploded form in FIG. 33, and in place in FIG. 34. The guidewire will allow the replacement of the first inserted cannula or access sheath 13, to be replaced with another access sheath (to be discussed) that is to be advanced along the placed guidewire 12.

Figure 35:
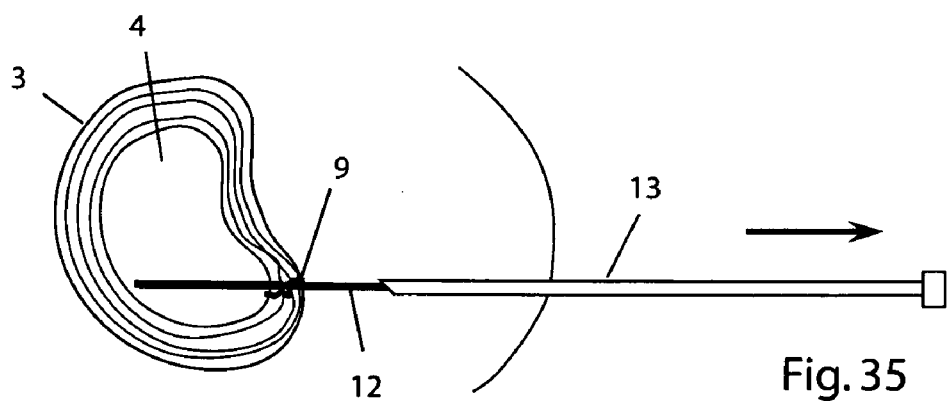
FIG. 35. An elevated view of the Guidewire of FIG. 34 remaining in place as the access cannula is removed from the patient.
Figure 36:
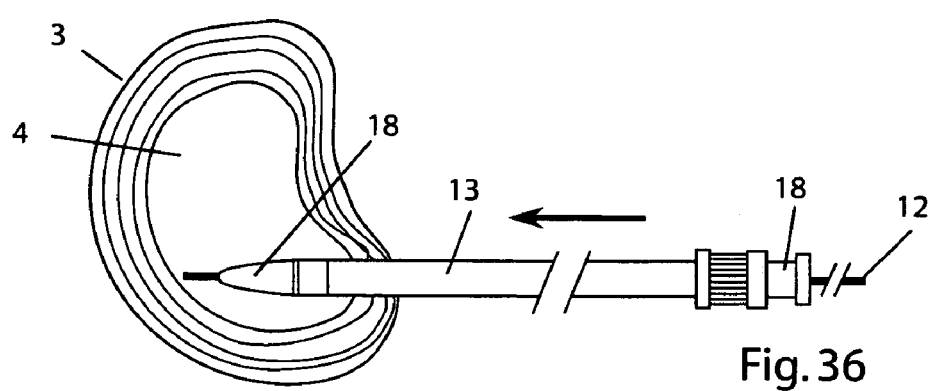
FIG. 36. An elevated view of the positioning of an Access sheath over the Guidewire of FIG. 35.

With reference to FIG. 35, after removal of either or both of the obturator 14 (from FIG. 32) or the cannula 13 (from FIG. 34), the guidewire 12 or wire-like element can be left in the puncture or defect 9 and may serve to guide an access sheath 13 for the delivery system 15 to the appropriate position at the target site. As depicted in FIG. 36, the access sheath 13 may optionally utilize at least one tissue dilator 18 (e.g. trocar, obturator, etc.) that is arranged to expand the initial opening or defect 9 in the annulus 3 to a size capable of allowing the penetration of the access sheath 13, and associated delivery device housing a closure device into the opening created. It is recognized that a series of tissue dilators 18 and or access sheaths, increasing in size may be utilized to achieve an aperture of greater size in the tough annulus layer 3 than the original opening or defect 9 created in FIG. 31. In use, the tissue dilator 18 is inserted through the access sheath 13, and extends therefrom, forming a tapered snout that serves to expand the tissue, such as annulus 3 to the point where the access sheath 13 may be inserted.

As the access sheath 13 is positioned over the guidewire 12 and advanced into the aperture, as seen in FIG. 36, various techniques for ensuring the positioning of the device are available. For example, radiopaque markers (not shown) can be used to properly locate the sheath at the ideal position. Alternatively, other location detector mechanisms, as described previously, may be utilized.

Figure 37:
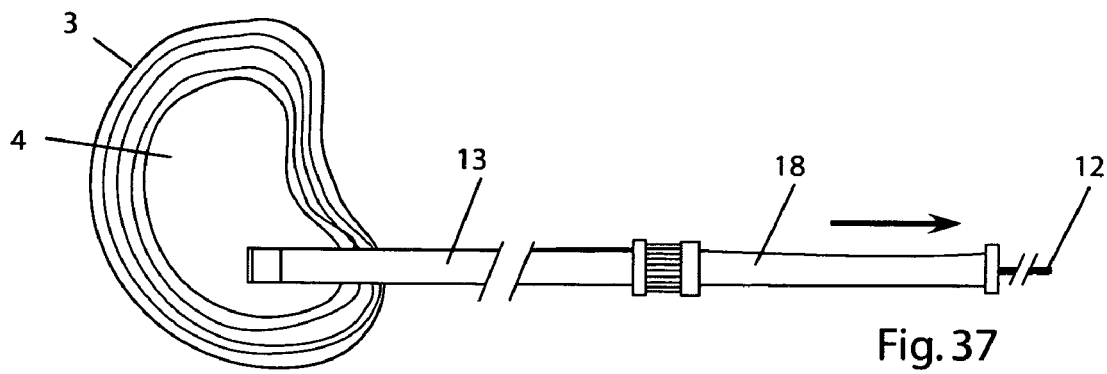
FIG. 37. An elevated view of the Access sheath of FIG. 36 as the obturator (e.g. dilator) and guidewire of FIG. 36 are removed.

In the embodiment where an access sheath 13 incorporates an expandable or reconfigurable locking member 22 located at or near the distal end of the access sheath 13, the locking member 22 may also function as a location detector. In this manner, the actuation of the expandable or reconfigurable locking member may provide feedback or tactile sensations to the operator as to the type of tissue is being encountered, thereby allowing the operator to distinguish placement within the annulus 3 from placement within the nucleus 4. For the practice of this embodiment, it is preferred that the tissue dilator 18 and wire 12 be removed, as depicted in FIG. 37, leaving the access sheath 13 penetrating into the disc 16.

Figure 38:
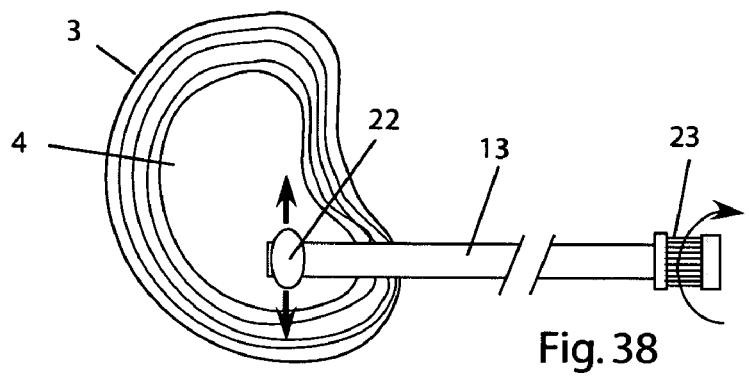
FIG. 38. An elevated view of the activation or deployment of a location detector on the access cannula of FIG. 37.

As shown in FIG. 38, the realization of location detection may be achieved by deploying or reconfiguring the locking mechanism 22, by such as through the action of actuation mechanism 23. The actuation of the expandable or reconfigurable locking member 22 may be accomplished by various means (e.g. inflation, or mechanical actuation). As shown in FIG. 38, with this particular embodiment, actuation mechanism 23 is preferably located at the proximal end of the access sheath 13, and may be rotatable, and upon rotation, or in the case of an inflation port, upon delivery of an inflation charge, serves to actuate the locking member 22 at the distal tip of the sheath 13, causing the locking member 22 to expand via one of several mechanisms (e.g. balloon expansion, nitinol wings, etc.). In the instance where the actuation of the locking member 22 were to cause the locking member to encounter tough annulus tissue, this would serve as an indicator to the operator that the sheath must be advanced into the nucleus, until softer nucleus material is encountered, allowing easier expansion of the locking member 22. The mechanisms (e.g. balloon, nitinol wings, etc.) may also be used to prepare a physical space for the delivery of the device. For example, the balloon can be inflated to a large initial diameter to stretch or otherwise move tissue. Then the balloon can later be reduced in size to provide a deployment space for a component of the device. In the case of an embodiment having another expandable mechanism, such as nitinol wings, the expandable mechanism may be expanded and optionally through the rotation or translation of the access sheath, or other instrument upon which the mechanisms are mounted, a physical space can be created to allow for proper deployment of the remaining components of the device.

Figure 39:
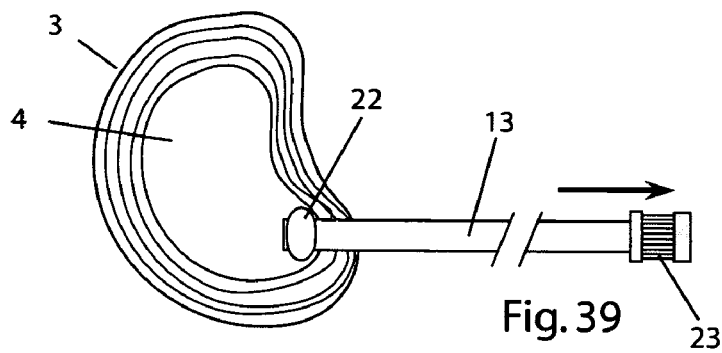
FIG. 39. An elevated view of the retraction of the access sheath and deployed location detector of FIG. 38.
Figure 40:
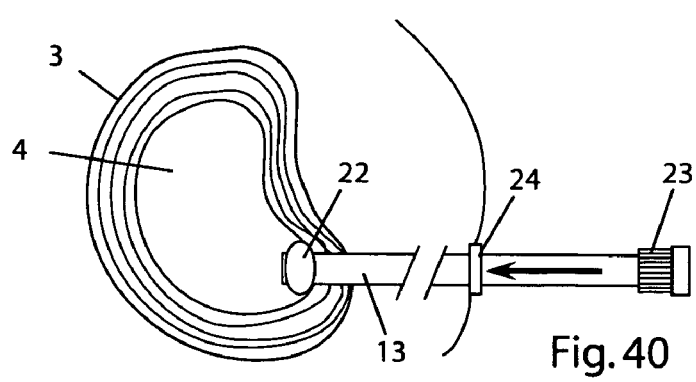
FIG. 40. An elevated view of a deployment of a locking ring on the access sheath of FIG. 39.

Upon successful deployment of the locking member 22, and with reference to FIG. 39, the operator or surgeon may retract the access sheath 13 until resistance is felt as the locking member 22 traverses relatively freely through a portion of the nucleus 4 and encounters the annulus 3 thereby providing the resistance to further retraction. Optionally, and as shown in FIG. 40, a locking mechanism (e.g. a locking ring) 24 may be advanced down the access sheath 13 in a proximal to distal fashion toward the puncture (i.e., against the skin or tissue of the patient) to stabilize the access sheath 13.

Figure 41:
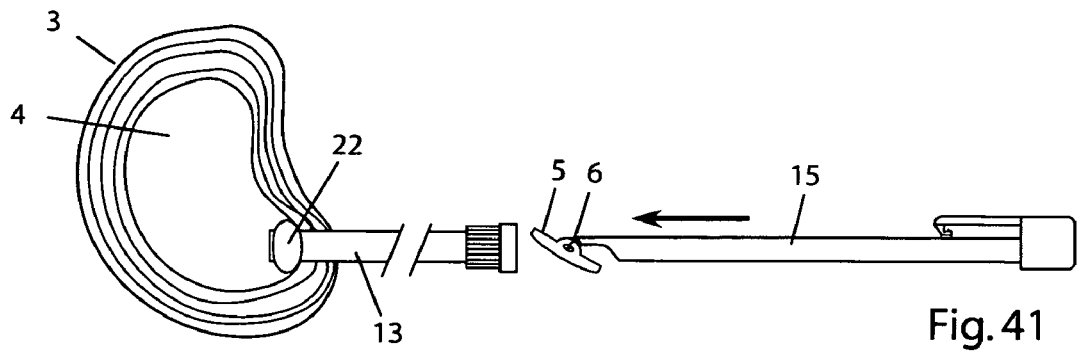
FIG. 41. An elevated view of the access sheath of FIG. 40 and depicting the introduction of the delivery system into the access sheath.

As shown in FIG. 41, the delivery device 15 containing the closure device may now be inserted into the access sheath 13. In a preferred embodiment, the anchoring element 5 is at the distal end of the delivery device 15, and is temporarily maintained in alignment with the axis of the access sheath 13 to allow passage into the sheath. For example, the anchoring element may be affixed to a flexible connector element 6 (e.g. a filament, suture, etc.), wherein the flexible connector element allows the anchoring element 5 to freely conform to varying angles. As shown here, the delivery device 15 is arranged to be inserted through the access sheath 13, and advanced through the sheath until the delivery device is fully inserted.

Figure 42:
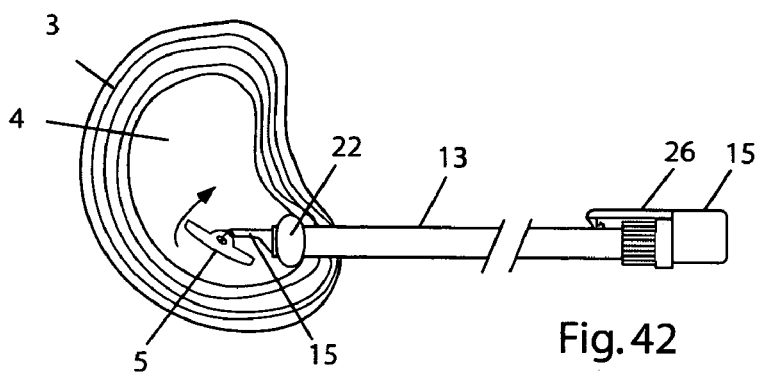
FIGS. 42-47. Elevated profile views of the deployment and securement of the closure device of the delivery system of FIG. 41.

As shown by FIG. 42, upon full insertion of the delivery device 15 into the access sheath 13, the anchoring element 5 or elements, are deployed into the nucleus 4. Once free from being aligned with the axis of the access sheath 13, the anchor element 5 is able to recover to its original orientation or another orientation by pivoting at least slightly on the flexible connector element 6. Furthermore, additional mechanisms can be used to ensure the anchor element is deployed in such a manner that retraction into the introducer sheath 13 will not occur. For example, the incorporation of one-way valves located at the distal end of the access sheath 13, or alternatively small nitinol deflection fingers that would force the anchor element 5 off to the side, may be utilized to prevent the anchoring element from being retracted back into the access sheath 13.

Also with reference to FIG. 42, a locking tab may be incorporated onto the proximal end of the delivery device 15. As the delivery device 15 is fully inserted, the locking tab encounters and passes the proximal end of the access sheath 13, traveling in a proximal to distal direction.

Figure 43:
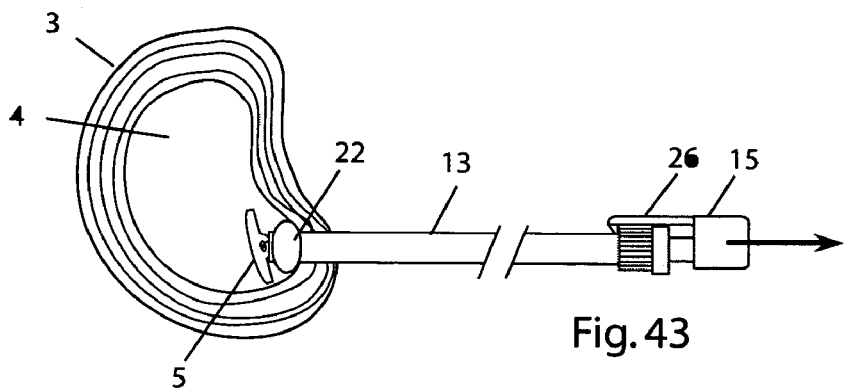
Figure 44:
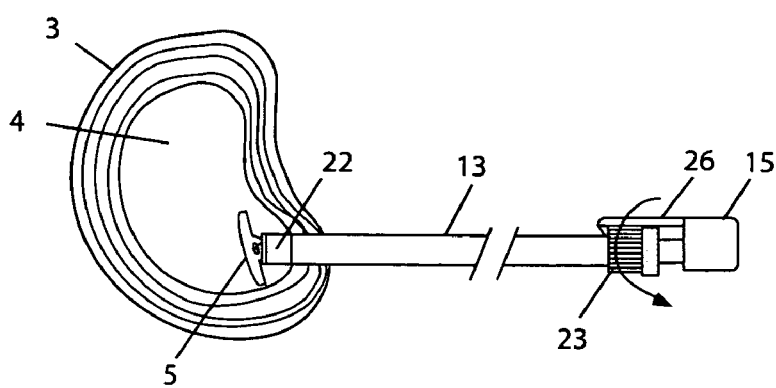

As shown in FIG. 43, the locking tab 26 is capable of one-way movement over the access sheath's 13 proximal end, and will then become engaged with the access sheath as the delivery device 15 is retracted at least partially from the patient and out of the access sheath 13. This retraction causes the locking tab 26 to engage or lock onto the access sheath 13, such that the access sheath and the delivery device are now interlocked as one unit. While interlocked and one unit, the anchor 5 may be placed under tension by the flexible connector element 6 as the anchor encounters the locking member 22 in an expanded state. Alternatively, and as shown in FIG. 44, the locking member 22 may be de-actuated, such as through the action of actuation mechanism 23, such that it reverts back to its original, non-expanded state.

Figure 45:
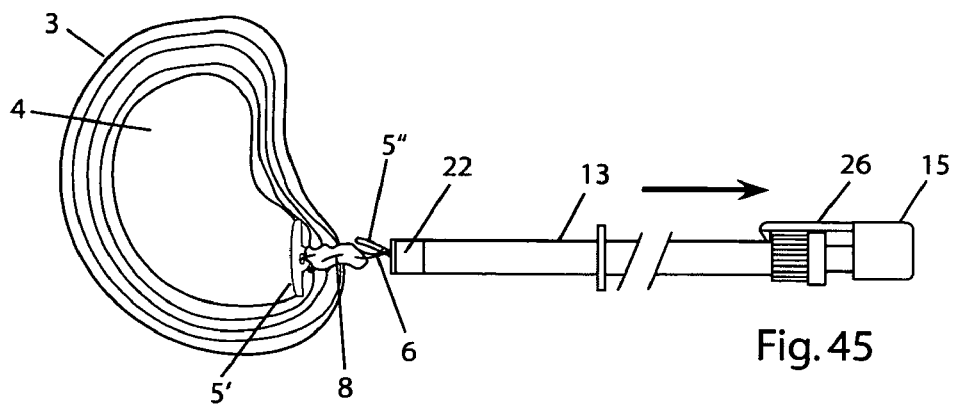

As shown in FIG. 45, the access sheath 13 and delivery device 15 are removed as one unit. The retraction of the delivery device places tension upon the anchoring element 5 through the flexible connector element 6. This tension causes the anchoring element to position itself against the interior surface of the annulus 3 at the location of the defect 9 or aperture. Various embodiments of a closure device can be utilized in the practice of this invention, as have already been described. As depicted in FIG. 45, an intermediate component 8 in the form of a sealing material associated with a portion of the flexible connecter element 6 may be deposited within the annulus wall 3. Continued retraction of the access sheath 13 and delivery device 15 results in the deployment of a second anchoring element 5". By altering characteristics necessary for the various embodiments of the closure device, such as manipulating the length of the connector element 6, and varying the placements of the access sheath 13, the deployment of the various described embodiments of the closure device can be achieved.

Figure 46:
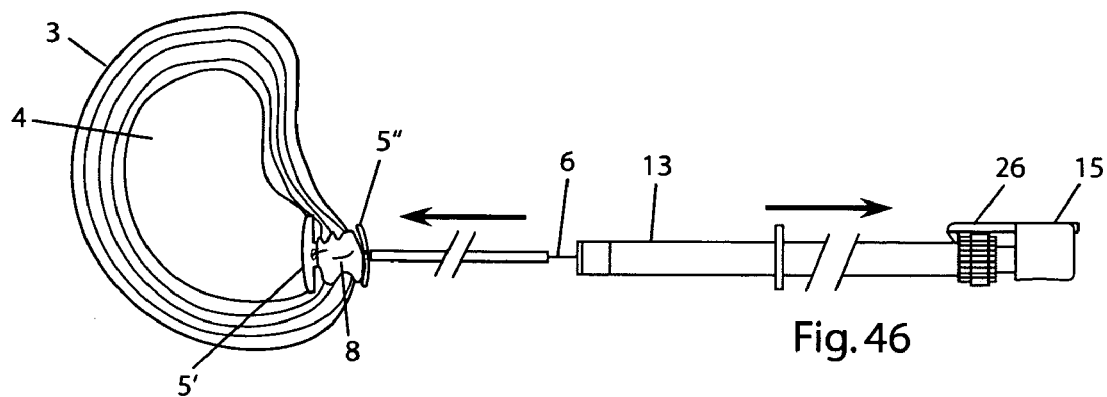

As shown in FIG. 46, the proximal end of the flexible connector element 6 or suture is preferably stored within the delivery device 15, for example, in a coil like system, and self-deploys from the delivery device as the device is withdrawn from the puncture, all the while maintaining tension upon the originally deployed anchoring element 5. As can be seen in FIG. 46, the tension may be maintained through the connector element 6 by the retraction of the delivery device 15. Further, a tamper or other instrument, may be utilized to push down upon a second (proximal) anchoring element 5", and enable the placement of a fastening or holding element 17.

Figure 47:
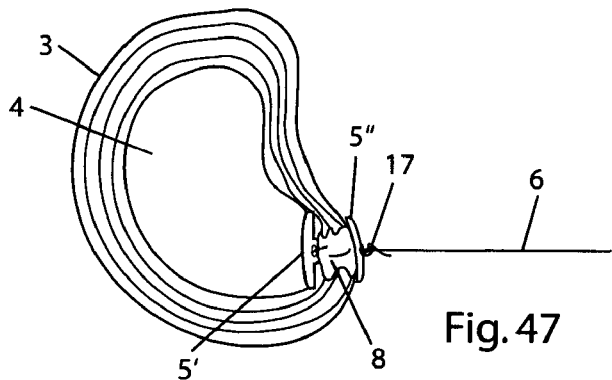

As shown in FIG. 47, a fastening element 17 may be positioned against the outside of the puncture in the annulus 3, or preferably against the proximal anchor 5". Alternatively, the fastening element 17 may be placed outside of the patient and against the skin where the connector element enters the tissue. The fastening element could be any of a variety of tension maintaining devices, for example, a locking washer, a knot, or a variety of elements or combination of elements may be utilized. In this embodiment, a small-elongated tube may be used to position the fastening element 17 against the closure device and the tube is preferably removed after securing the fastening element 17. Alternatively, a pulley configuration could be used with a fastening element 17 in the form of a sliding locking knot, and would not require the use of an elongated tube to apply tension, as the operator applies tension simply by pulling on the connector element 6, whereby the pulley arrangement and sliding locking knot are arranged to maintain that tension.

After the closure device is fully positioned at the tissue defect 9, any extraneous connector element 6 or suture may be removed. As appropriate any of the embodiments of the device described in the specification may be used to deliver various medications at the puncture site and to the surrounding tissues.

Accessory Tools to Assist in the Practice of the Present Invention

Figure 50:
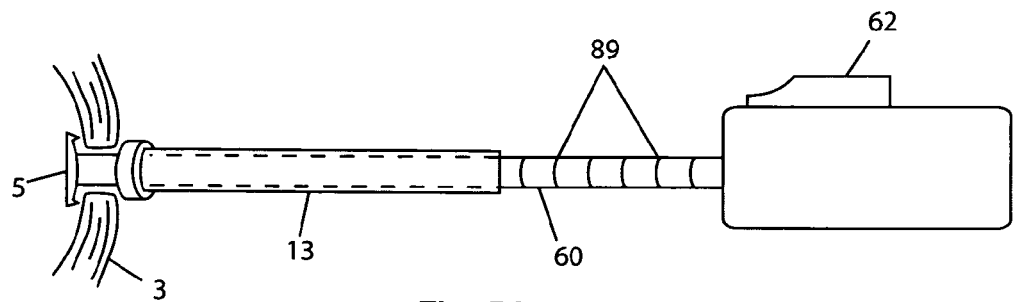
FIGS. 50-53. Depictions of accessory instruments that may be utilized in the practice of the present invention

As discussed previously, an anchor sizing and depth probe instrument may be employed to assist in ensuring proper placement of the closure devices of the present invention. As can be seen with reference to FIG. 50, the depth probe instrument consists of a probe 60 with a retractable anchor 5 at the distal end. The distal end of the probe, with the anchor retracted, is inserted through the annulus and into the defect, whereupon the anchor 5 may be deployed by means of trigger mechanism 62, causing the anchor to rotate to a deployed state as shown in FIG. 50. By manipulating the probe and anchor into position against the annulus tissue, the operator may detect whether the anchor will become adequately lodged against the annulus, giving an indication of whether or not the size of the anchor is adequate. If necessary, the trigger mechanism 62 may be reversed, retracting the anchor 5 back into an obscured position, and the probe removed. Various probes having anchors of different sizes may be employed if necessary. Additionally, the depth of the location of the anchor may be determined by use of reference markings 89 on the probe, which may be referenced against a known mark, or alternatively by a drop down gauge inserted through the probe, which may be incorporated directly into the depth probe instrument, or alternatively deployed as a separate component.

Figure 51:
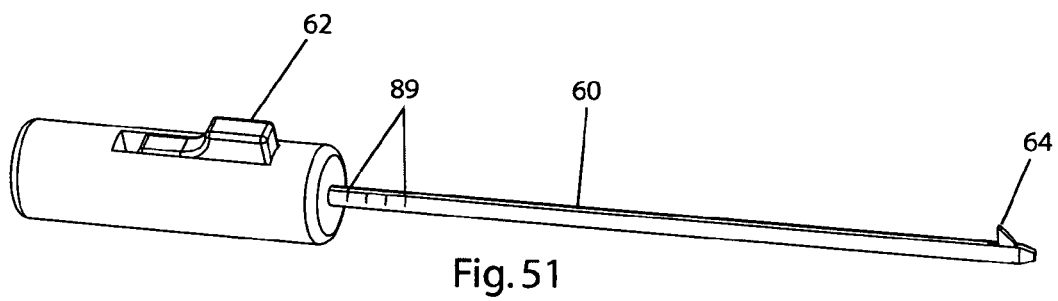

Additionally, a dissecting tool, as seen in FIG. 51, may be employed to separate the tissues adjacent the defect to be closed in the annulus. Similar to the depth probe described above, the dissection tool consists of a probe 60 with reference markings or of known length, having at its distal end a reconfigurable and/or retractable element 64, such as a finger, wing, balloon, etc., that may be deployed inside the defect or adjacent the defect, in order to separate the tissues, thereby creating a space for the subsequent deployment of the anchor of the closure device. After insertion of the probe, the triggering mechanism 62 may be operated, causing the deployment of the reconfigurable element 64. In an embodiment where the reconfigurable element is a finger or jaw, extending in one axis, or less than entirely circumferentially, rotation of the probe may be necessary to dissect the tissues in a given radius. In an embodiment where the reconfigurable element is deployed in many directions, such as in the expansion of a balloon, no rotation may be necessary. After dissection, the triggering mechanism 62 is reversed, withdrawing the reconfigurable element 64 back into an "at rest" state, such as within the probe, and the probe 60 withdrawn.

Figure 52:
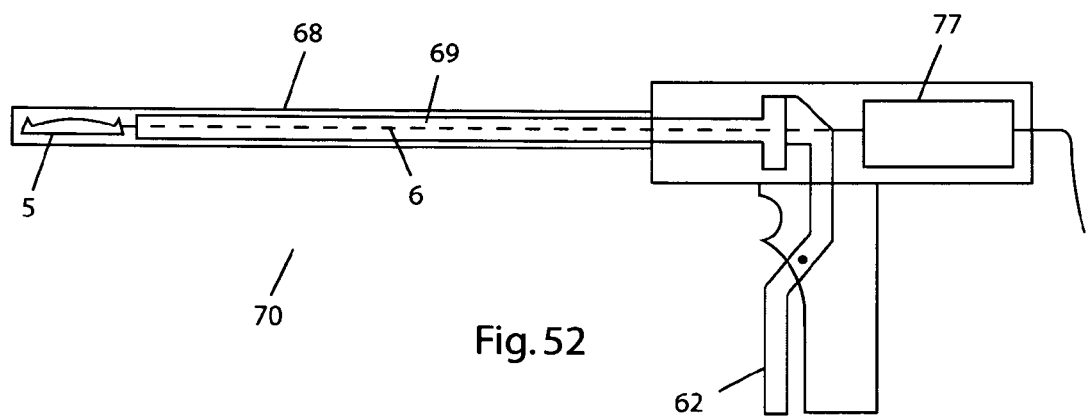

As can be seen with reference to FIG. 52, the deployment of the closure device may be facilitated by a deployment system 70. The deployment system may be actuated by means known in the art, such as a trigger mechanism 62. Upon actuation, the deployment of the closure device may be achieved, where the anchor 5 is ejected from the cannula 68 by action of tamping rod 69, connected to connecting element 6, and optionally, additional closure device components (e.g. plug material, locking mechanism, external anchor, etc.) contained within the cannula 68. Preferably, the deployment system includes a means of maintaining tension upon the connector element 6, shown here as a suture. The tensioning means 77 preferably is a friction grip which allows for a preset level of tension to be maintained, but allows slippage of the suture if tension is increased beyond a set level. Optionally, the tension mechanism may be a simple locking mechanism to grip the suture without allowing for slippage. It is recognized that the deployment system may also be capable of severing the suture or connector element to allow removal of the system, while leaving the closure device implanted. The suture may be severed upon actuation of triggering mechanism 62, or by other means.

Figure 53:
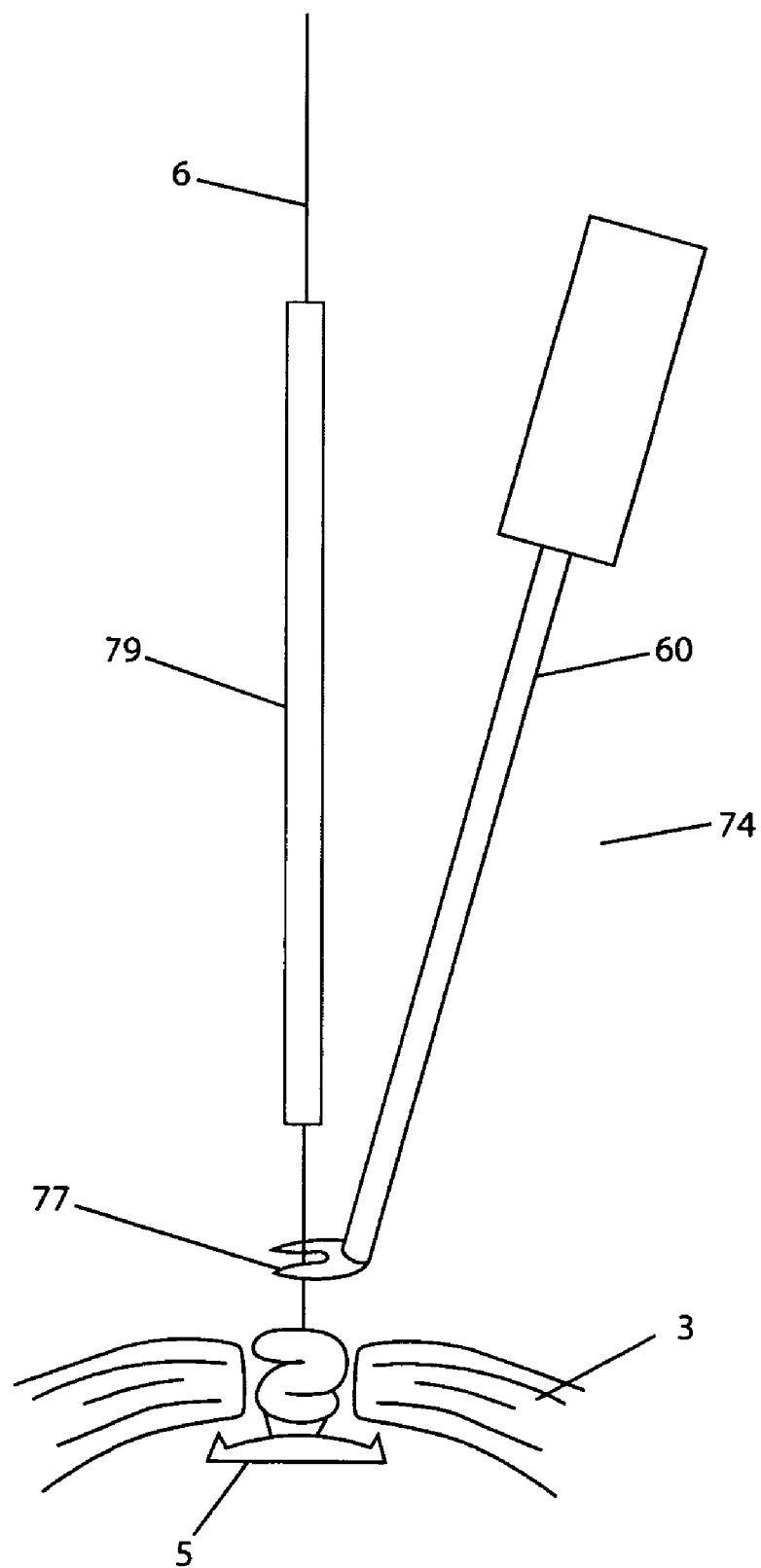

Alternatively, as depicted in FIG. 53, a distinct suture cutting tool 74 may be inserted into the opening to sever the connector element 6, at or near the defect site, in order to prevent excess suture or connecting element from causing complications. The cutting tool consists of a probe 60, having at its distal end a cutting edge 77, preferably a V-shaped cutting edge as shown. If necessary, a tamping tool 79 may be utilized to ensure correct placement of the closure device components (e.g. sealing plug materials, anchors, locking mechanism, etc.). While maintaining tension upon the suture, the tamping tool is adjusted to clear an opening above the closure device, and the cutting tool 74 may be directed into the working incision to reach close to the surgical site. Preferably, the cutting tool is advanced through the incision until the probe 60 encounters the annular wall, whereupon the cutting edge is employed to sever the suture or connecting element proximal to any locking mechanism. The severed portion of the connecting element may then be removed, along with the cutting tool. It is recognized that the cutting tool may utilize a retractable, articulating or recessed cutting edge, deployable by mechanisms similar to deployment mechanisms known in the art.

Thus since the invention disclosed herein may be embodied in other specific forms without departing from the spirit or general characteristics thereof, some of which forms have been indicated, the embodiments described herein are to be considered in all respects illustrative and not restrictive, by applying current or future knowledge. The scope of the invention is to be indicated by the appended claims, rather than by the foregoing description, and all changes which come within the meaning and range of equivalency of the claims are intended to be embraced therein.

TABLE 1

Examples Of Suitable Materials

Aliphatic polyesters
Bioglass
Cellulose
Chitin
Collagen

Types 1 to 20
Native fibrous
Soluble
Reconstituted fibrous
Recombinant derived
Copolymers of glycolide
Copolymers of lactide
Elastin
Fibrin
Glycolide/l-lactide copolymers (PGA/PLLA)
Glycolide/trimethylene carbonate copolymers (PGA/TMC)
Hydrogel
Lactide/tetramethylglycolide copolymers
Lactide/trimethylene carbonate copolymers
Lactide/ε-caprolactone copolymers
Lactide/σ-valerolactone copolymers
L-lactide/dl-lactide copolymers
Methyl methacrylate-N-vinyl pyrrolidone copolymers
Modified proteins
Nylon-2
PHBA/γ-hydroxyvalerate copolymers (PHBA/HVA)
PLA/polyethylene oxide copolymers
PLA-polyethylene oxide (PELA)
Poly(amino acids)
Poly(trimethylene carbonates)
Poly hydroxyalkanoate polymers (PHA)
Poly(alklyene oxalates)
Poly(butylene diglycolate)
Poly(hydroxy butyrate) (PHB)
Poly(n-vinyl pyrrolidone)
Poly(ortho esters)
Polyalkyl-2-cyanoacrylates
Polyanhydrides
Polycyanoacrylates
Polydepsipeptides
Polydihydropyrans
Poly-dl-lactide (PDLLA)
Polyesteramides
Polyesters of oxalic acid
Polyethylene Glycol
Polyethylene Oxide
Polyglycan Esters
Poly(Glycerol Sebacate)
Polyglycolide (PGA)
Polyiminocarbonates
Polylactides (PLA)
Poly-l-lactide (PLLA)
Polyorthoesters
Poly-p-dioxanone (PDO)
Polypeptides
Polyphosphazenes
Polysaccharides
Polyurethanes (PU)
Polyvinyl alcohol (PVA)
Poly-β-hydroxypropionate (PHPA)
Poly-β-hydroxybutyrate (PBA)
Poly-σ-valerolactone
Poly-β-alkanoic acids
Poly-β-malic acid (PMLA)
Poly-ε-caprolactone (PCL)
Pseudo-Poly(Amino Acids)
Starch
Trimethylene carbonate (TMC)

TABLE 1-continued

Examples Of Suitable Materials

Tyrosine based polymers
Alginate
Bone allograft or autograft
Bone Chips
Calcium
Calcium Phosphate
Calcium Sulfate
Ceramics
Chitosan
Cyanoacrylate
Collagen
Dacron
Demineralized bone
Elastin
Fibrin
Gelatin
Glass
Gold
Glycosaminoglycans
Hydrogels
Hydroxy apatite
Hydroxyethyl methacrylate
Hyaluronic Acid
Liposomes
Mesenchymal cells
Nitinol
Osteoblasts
Oxidized regenerated cellulose
Phosphate glasses
Polyethylene glycol
Polyester
Polysaccharides
Polyvinyl alcohol
Platelets, blood cells
Radiopacifiers
Salts
Silicone
Silk
Steel (e.g. Stainless Steel)
Synthetic polymers
Thrombin
Titanium
Tricalcium phosphate

TABLE 2

Examples of Biologically Active Agents

Adenovirus with or without genetic material
Alcohol
Amino Acids

L-Arginine
Angiogenic agents
Angiotensin Converting Enzyme Inhibitors (ACE inhibitors)
Angiotensin II antagonists
Anti-angiogenic agents
Antiarrhythmics Amiodarone
Lidocaine
Sotalol
Procainamide
Diltiazem
Anti-bacterial agents
Antibiotics Erythromycin
Penicillin
Imipenem
Zosyn
Cipro
Flagyl
Vancomycin
Anti-coagulants TABLE 2-continued Examples of Biologically Active Agents Heparin
Lovenox
Anti-Fungals
Anti-growth factors
Anti-inflammatory agents Dexamethasone
Prednisone
Aspirin
Hydrocortisone
Antioxidants
Anti-platelet agents Forskolin
GP IIb-IIIa inhibitors
eptifibatide
Anti-proliferation agents Rho Kinase Inhibitors
(+)-trans-4-(1-aminoethyl)-1-(4-pyridylcarbamoyl)
cyclohexane
Anti-rejection agents
Anti-restenosis agents Adenosine A2A receptor agonists
Rapamycin
Antisense
Anti-thrombogenic agents Argatroban
Fondaparinux
Hirudin
GP IIb/IIIa inhibitors
Anti-TNF
Anti-viral drugs
Arteriogenesis agents acidic fibroblast growth factor (aFGF)
angiogenin
angiotropin
basic fibroblast growth factor (bFGF)
Bone morphogenic proteins (BMP)
epidermal growth factor (EGF)
fibrin
granulocyte-macrophage colony stimulating factor (GM-CSF)
hepatocyte growth factor (HGF)
HIF-1
Indian hedgehog (Inh)
insulin growth factor-1 (IGF-1)
interleukin-8 (IL-8)
MAC-1
nicotinamide
platelet-derived endothelial cell growth factor (PD-ECGF)
platelet-derived growth factor (PDGF)
transforming growth factors alpha & beta (TGF-.alpha.,
TGF-beta.)
tumor necrosis factor alpha (TNF-.alpha.)
vascular endothelial growth factor (VEGF)
vascular permeability factor (VPF)
Bacteria
Beta blocker
Blood clotting factor
Bone morphogenic proteins (BMP)
Calcium channel blockers
Carcinogens
Cells Stem cells
Bone Marrow
Blood cells
Fat Cells
Muscle Cells
Umbilical cord cells
Chemotherapeutic agents 5-FU
Ceramide TABLE 2-continued Examples of Biologically Active Agents Cisplatin
Cyclophosphamide
Doxorubicin
Flutamide
Imatinib
Levamisole
Methotrexate
Mitomycin
Oxaliplatin
Paclitaxel
Tamoxifen
Taxol
Topotecan
Vinblastine
Cholesterol reducers
Chondroitin
Clopidegrel (e.g., plavix)
Collagen Inhibitors
Colony stimulating factors
Coumadin
Cytokines prostaglandins
Dentin
Etretinate
Genetic material
Glucosamine
Glycosaminoglycans
GP IIb/IIIa inhibitors L-703,081
Granulocyte-macrophage colony stimulating factor (GM-CSF)
Growth factor antagonists or inhibitors
Growth factors Autologous Growth Factors
Bovine derived cytokines
Cartilage Derived Growth Factor (CDGF)
Endothelial Cell Growth Factor (ECGF)
Epidermal growth factor (EGF)
Fibroblast Growth Factors (FGF)
Hepatocyte growth factor (HGF)
Insulin-like Growth Factors (e.g. IGF-I)
Nerve growth factor (NGF)
Platelet Derived Growth Factor (PDGF)
Recombinant NGF (rhNGF)
Tissue necrosis factor (TNF)
Tissue derived cytokines
Transforming growth factors alpha (TGF-alpha)
Transforming growth factors beta (TGF-beta)
Vascular Endothelial Growth Factor (VEGF)
Vascular permeability factor (VPF)
Acidic fibroblast growth factor (aFGF)
Basic fibroblast growth factor (bFGF)
Epidermal growth factor (EGF)
Hepatocyte growth factor (HGF)
Insulin growth factor-1 (IGF-1)
Platelet-derived endothelial cell growth factor (PD-ECGF)
Tumor necrosis factor alpha (TNF-.alpha.)
Growth hormones
Heparin sulfate proteoglycan
HMC-CoA reductase inhibitors (statins)
Hormones Erythropoietin
Immoxidal
Immunosuppressant agents
Immune modulator agents
Inflammatory mediator
Insulin
Interleukins
Interlukins Interlukin-8 (IL-8)
Lipid lowering agents
Lipo-proteins
Low-molecular weight heparin
Lymphocites
Lysine TABLE 2-continued Examples of Biologically Active Agents MAC-1
Methylation inhibitors
Morphogens Bone morphogenic proteins (BMPs)
Nitric oxide (NO)
Nucleotides
Peptides
Polyphenol
PR39
Proteins
Prostaglandins
Proteoglycans Perlecan
Radioactive materials Iodine - 125
Iodine - 131
Iridium - 192
Palladium 103
Radio-pharmaceuticals
Secondary Messengers Ceramide
Signal Transduction Factors
Signaling Proteins
Somatomedins
Statins
Stem Cells
Steroids
Sulfonyl
Thrombin
Thrombin inhibitor
Thrombolytics
Ticlid
Tumor necrosis factor
Tyrosine kinase Inhibitors ST638
AG-17
Vasodilator Histamine
Forskolin
Nitroglycerin
Vitamins E
C
Yeast
*Ziyphi fructus*

What is claimed is:

1. A system for repairing a defect or opening in the wall of the annulus of a living being, said system comprising:
   (a) an access sheath arranged to be placed through the opening;
   (b) a location detector arranged for providing a signal indicative of the location of said location detector relative to the opening, at least a portion of said location detector being near a distal end of said access sheath; and
   (c) a treatment device arranged to be positioned at said location to repair said defect or opening, said treatment device comprising at least one anchoring member and at least one connector element, at least one of said anchoring members comprising a sealing member arranged to prevent the passage of fluid through said defect or opening, wherein said sealing member is folded into pleats upon application of tension upon said connector element.

2. The system of claim 1, wherein said connector element comprises a resorbable suture.

3. The system of claim 1, wherein said treatment device further comprises an intermediary component associated with said connector element.

4. The system of claim 3, wherein said intermediary component comprises a collagen plug.

5. The system of claim 1, wherein said treatment device further comprises a locking member.

6. The system of claim 5, wherein said locking member is selected from the group consisting of a button, knot, and washer.

7. The system of claim 5, wherein said locking member is arranged to maintain said connector element in tension.

8. The system of claim 1, wherein said system additionally comprises a delivery device arranged to be inserted through said access sheath.

9. The system of claim 8, wherein said delivery device is arranged to house said treatment device.

10. The system of claim 9, wherein said location detector is arranged integrally to said delivery device.

11. The system of claim 10, wherein said location detector comprises an electronic sensor that senses an adjacent tissue at a distal end of said delivery device, said electronic sensor selected from the group consisting of optical sensor and pressure sensor.

12. The system of claim 10, wherein said location detector comprises a reconfigurable member.

13. The system of claim 12, wherein said reconfigurable member is inserted in a first configuration, and upon actuation is reconfigured to a second configuration.

14. The system of claim 13, wherein said reconfigurable member is selected from the group consisting of balloon, wing, and finger.

15. The system of claim 10, wherein said location detector is arranged to function as a locking member.

16. The system of claim 15, wherein said locking member is arranged to prevent movement of said delivery device from said desired location.

17. The system of claim 10, wherein said location detector provides said perceptible signal by a tactile sensation.

18. The system of claim 10, wherein said location detector is arranged to distinguish between deployment of said treatment device within an annulus, or within a nucleus of an intervertebral disc.

19. The system of claim 10, wherein said location detector comprises a plurality of graduated markings on a proximal end of said delivery device.

20. The system of claim 1, wherein said location detector comprises a separate detector passageway lumen through said access sheath.

21. The system of claim 20, wherein a detection probe is directed through said detector passageway lumen and exits said access sheath at a distal end, wherein said probe contacts adjacent tissue.

22. The system of claim 1, wherein said at least one anchoring member further comprises at least two anchoring members comprising a proximal anchor and a distal anchor being connected by said filament.

23. The system of claim 22, wherein said proximal anchor is arranged to be delivered to an outside aspect of an annulus, and said distal anchor is arranged to be delivered to an inside aspect of said annulus.

24. The system of claim 1, wherein at least a portion of said treatment device is resorbable.

25. The system of claim 24, wherein said resorbable material is arranged to deliver a biologically active agent.

26. The system of claim 24, wherein said resorbable treatment device comprises a porous tissue matrix material.

27. The system of claim 26, wherein said porous tissue matrix material is arranged to induce cellular ingrowth.

28. The system of claim 1, wherein said sealing member is arranged to swell in contact with body fluids.

29. The system of claim 28, wherein said sealing member comprises a collagen plug.

30. The system of claim 1, wherein said at least one anchoring member is arranged to be attached to said at least one connector element by at least one attachment point.

31. The system of claim 30, wherein said at least one attachment point is located off-center from said at least one anchoring member.

32. The system of claim 1, wherein said system additionally comprises at least one accessory tool selected from the group consisting of: depth probe, size probe, dissection tool, and cutting tool.

33. A system for repairing a defect or opening in the wall of the annulus of a living being, said system comprising:
(a) an access sheath arranged to be placed through the opening;
(b) a location detector arranged for providing a signal indicative of the location of the location detector relative to the opening, at least a portion of said location detector being near a distal end of said access sheath; and
(c) a treatment device arranged to be positioned at said location to repair said defect or opening, said treatment device comprising at least one anchoring member and at least one connector element, at least one of said anchoring members comprising a sealing member arranged to prevent the passage of fluid through said defect or opening, wherein said sealing member comprises a hinge and a plurality of arms.

34. A system for repairing a defect or opening in the wall of the annulus of a living being, said system comprising:
(a) an access sheath arranged to be placed through the opening;
(b) a location detector arranged for providing a signal indicative of the location of the location detector relative to the opening, at least a portion of said location detector being near a distal end of said access sheath; and
(c) a treatment device arranged to be positioned at said location to repair said defect or opening, said treatment device comprising at least one anchoring member and at least one connector element, at least one of said anchoring members comprising a sealing member arranged to prevent the passage of fluid through said defect or opening, wherein said at least one anchoring member is arranged to be attached to said at least one connector element by at least one attachment point, and wherein said at least one attachment point is located off-center from said at least one anchoring element.

* * * * *